US008660517B2

(12) United States Patent
DeMont et al.

(10) Patent No.: US 8,660,517 B2
(45) Date of Patent: Feb. 25, 2014

(54) PERSONAL ASSISTANCE MONITORING SYSTEM

(76) Inventors: Jason Paul DeMont, Fairview, TX (US); David Michael Lazoff, Berkeley, CA (US)

( * ) Notice: Subject to any disclaimer, the term of this patent is extended or adjusted under 35 U.S.C. 154(b) by 0 days.

(21) Appl. No.: 13/558,414

(22) Filed: Jul. 26, 2012

(65) Prior Publication Data
US 2013/0090083 A1 Apr. 11, 2013

Related U.S. Application Data

(60) Provisional application No. 61/544,796, filed on Oct. 7, 2011, provisional application No. 61/548,268, filed on Oct. 18, 2011.

(51) Int. Cl.
*H04M 11/04* (2006.01)
*H04M 3/00* (2006.01)
(52) U.S. Cl.
USPC .......... 455/404.1; 455/419; 455/420; 379/38; 379/39; 379/40
(58) Field of Classification Search
USPC ...................................... 455/404.1
See application file for complete search history.

(56) References Cited

U.S. PATENT DOCUMENTS

| | | | |
|---|---|---|---|
| 5,115,224 A | 5/1992 | Kostusiak et al. | |
| 5,305,370 A | 4/1994 | Kearns et al. | |
| 5,505,199 A | 4/1996 | Kim | |
| 5,742,233 A | 4/1998 | Hoffman et al. | |
| 6,044,257 A | 3/2000 | Boling et al. | |
| 6,166,639 A | 12/2000 | Pierce et al. | |
| 6,169,484 B1 | 1/2001 | Schuchman et al. | |
| 6,208,897 B1 | 3/2001 | Jorgenson | |
| 6,307,481 B1 | 10/2001 | Lehrman | |
| 6,433,690 B2 * | 8/2002 | Petelenz et al. | 340/573.1 |
| 6,551,252 B2 | 4/2003 | Sackner | |
| 6,553,256 B1 | 4/2003 | Jorgenson | |
| 6,611,783 B2 | 8/2003 | Kelly, Jr. et al. | |
| 6,819,247 B2 * | 11/2004 | Birnbach et al. | 340/573.1 |
| 7,123,758 B2 | 10/2006 | Jeung | |
| 7,231,200 B2 | 6/2007 | Jenkins | |

(Continued)

OTHER PUBLICATIONS

Angel Med Guardian System Web Page, http://www.angel-med.com/index.php/patients-families/our-solution.html, copied on Jul. 25, 2012.

(Continued)

*Primary Examiner* — Huy C Ho
(74) *Attorney, Agent, or Firm* — Kaplan Breyer Schwarz & Ottesen, LLP.

(57) ABSTRACT

A personal assistance monitor for estimating whether a person needs assistance or not, and for requesting assistance, when appropriate. Some embodiments of the present invention can request help for a person even if the person is unconscious or paralyzed. The illustrative embodiment comprises two bracelets—one is worn on a person's right wrist and the other is worn on the left wrist. Each bracelet comprises an acceleration sensor that detects the acceleration of the wrist to which it is affixed. The measures of motion detected by both bracelets are analyzed for insight into the person's well-being. When the illustrative embodiment estimates that the person needs assistance, the illustrative embodiment prompts the person to decline assistance. When the person declines assistance, the illustrative embodiment continues monitoring the person. In contrast, when the person fails to decline the offer of assistance, the illustrative embodiment requests help.

26 Claims, 19 Drawing Sheets

(56) References Cited

U.S. PATENT DOCUMENTS

| | | |
|---|---|---|
| 7,384,398 B2 | 6/2008 | Gagnadre |
| 7,420,472 B2 * | 9/2008 | Tran .................. 340/573.1 |
| 7,586,418 B2 | 9/2009 | Cuddihy et al. |
| 7,879,026 B2 | 2/2011 | Estes et al. |
| 7,916,066 B1 | 3/2011 | Osterweil |
| 7,941,876 B2 * | 5/2011 | Ferber ........................ 2/465 |
| 8,115,641 B1 | 2/2012 | Dempsey |
| 8,116,724 B2 * | 2/2012 | Peabody .................. 455/404.2 |
| 8,179,268 B2 | 5/2012 | Gannot et al. |
| 8,217,795 B2 | 7/2012 | Carlton-Foss |
| 8,337,431 B2 | 12/2012 | Heruth et al. |
| 8,350,707 B2 | 1/2013 | Needham et al. |
| 8,364,221 B2 | 1/2013 | Mannheimer et al. |
| 2003/0027547 A1 | 2/2003 | Wade |
| 2004/0094613 A1 | 5/2004 | Shiratori |
| 2006/0282021 A1 | 12/2006 | DeVaul |
| 2008/0129518 A1 | 6/2008 | Carlton-Foss |
| 2009/0322540 A1 | 12/2009 | Richardson |
| 2010/0298660 A1 | 11/2010 | McCombie |
| 2010/0298661 A1 * | 11/2010 | McCombie et al. ......... 600/301 |
| 2011/0025493 A1 | 2/2011 | Papadopoulos |

OTHER PUBLICATIONS

Medical Alarm, Wikipedia, http://en.wikipedia.org/wiki/Medical_alarm, copied on Jul. 25, 2012.

Healthlinks (brochure), www.healthlinksus.com (publication date unknown).

High-Tech Aging: Tracking Seniors' Every Move, Jennifer Ludden, National Public Radio, Aug. 23, 2010.

* cited by examiner

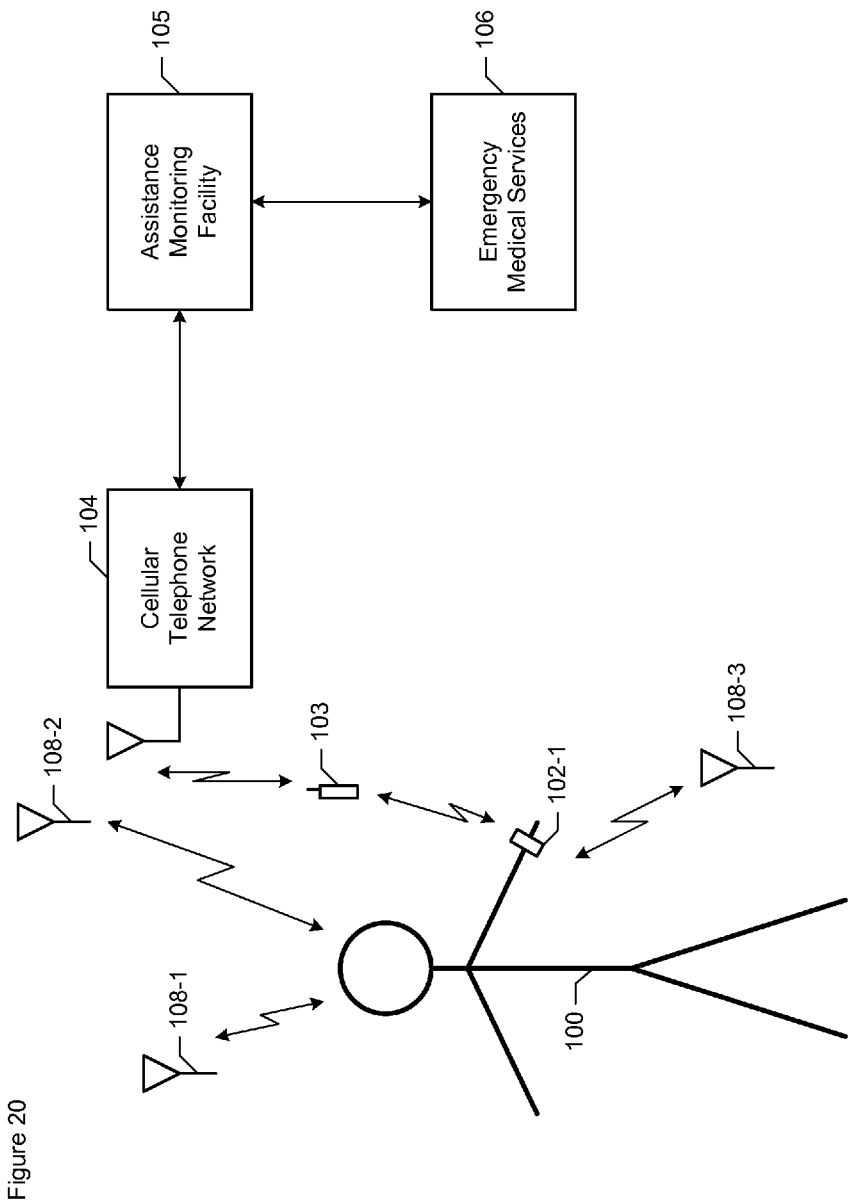

PERSONAL ASSISTANCE MONITORING SYSTEM

REFERENCE TO RELATED APPLICATIONS

This application claims the benefit of:
1. U.S. Provisional Application No. 61/544,796, filed Oct. 7, 2011, and
2. U.S. Provisional Application No. 61/548,268, filed Oct. 18, 2011, both of which are incorporated by reference. In any case in which this specification is inconsistent with either provisional application, this specification prevails.

FIELD OF THE INVENTION

The present invention relates to medical devices, in general, and in particular to an apparatus for monitoring the well-being of a person and for transmitting a request for assistance when the person needs assistance.

BACKGROUND OF THE INVENTION

One of the hazards of living alone, especially for seniors, is the possibility of a medical emergency, such as a fall, that renders the person unable to reach a telephone and call for help. To address this problem, personal assistance monitoring systems have been invented and marketed.

One popular personal assistance monitoring system is the Lifeline Medical Alert system, which comprises a pendant that is worn around the person's neck, and a device that comprises a two-way speaker that is attached to a wireline telephone. When the person suffers a medical emergency, he or she can push a button on the pendant, which transmits a radio signal that prompts the device to place a call, via the wireline telephone, to an assistance monitoring facility. A call center agent answers the call, and attempts to ascertain, via the two-way speaker, whether the person needs assistance. When the person indicates that he or she needs assistance, the agent dispatches emergency medical services to the person's residence.

Personal assistance monitors in the prior art are valuable and have undoubtedly saved lives, but they have costs and disadvantages.

SUMMARY OF THE INVENTION

The present invention provides a technique for estimating whether a person needs assistance, and for transmitting a request for assistance, when appropriate, without some of the disadvantages of personal assistance monitoring systems in the prior art. For example, some embodiments of the present invention can determine that a person needs assistance regardless of whether the person is awake, asleep, conscious, unconscious, functioning, or paralyzed and can transmit a request for assistance for the person without the person's participation.

The present invention is based on the insight that a person's movements, when measured and analyzed carefully in the context of other facts about the person, reveal a great deal about their well-being. The illustrative embodiment comprises two bracelets one is worn on a person's right wrist and the other is worn on the left wrist. Each bracelet comprises a motion sensor that detects the motion of the wrist to which it is affixed. The illustrative embodiment also comprises sensors that measure other facts about the person (e.g., the attitude of the person's body, the blood oxygen saturation level, the location of the person, etc.) and facts about the environment surrounding the person (e.g., the ambient light level, the ambient sound level, etc.). The bracelets and other sensors are worn by the person continuously. The motion detected by both bracelets, the facts about the person, and the facts about the environment are continually analyzed—both day and night—to generate an estimate of the whether the person needs assistance.

When the estimate of whether the person needs assistance indicates that the person does need assistance, the illustrative embodiment prompts the person to decline assistance. When the person declines assistance, the illustrative embodiment notes its error, adjusts the parameters it uses for generating the estimate of whether the person needs assistance, and continues monitoring the person.

In contrast, when the person does, in fact, require assistance, by failing to decline the offer of assistance, the illustrative embodiment transmits a request for assistance.

The illustrative embodiment comprises: receiving, from a motion sensor, a measure of motion of a location on a person's body; generating, by a processor, a motion profile based on the measure of motion; when the motion profile exhibits a sign of distress, generating, with a first output device, a prompt for the person to decline assistance; and when the person fails to decline assistance, transmitting, with a second output device, a request for assistance for the person.

BRIEF DESCRIPTION OF THE FIGURES

FIG. 20 depicts a schematic diagram of the fourth alternative embodiment of the present invention, which is used in conjunction with person 100.

DETAILED DESCRIPTION

Figure 1:
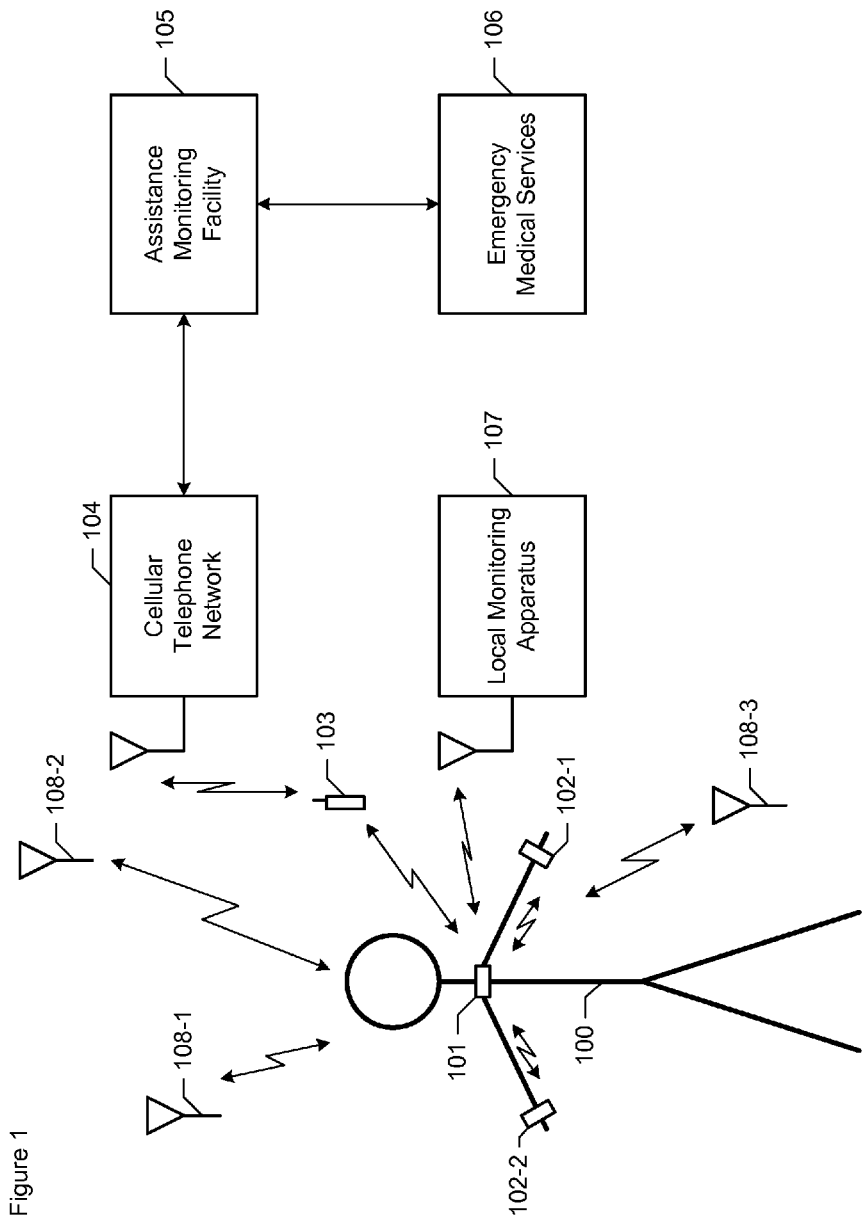
FIG. 1 depicts a schematic diagram of the illustrative embodiment of the present invention, which is used in conjunction with person 100.

FIG. 1 depicts a schematic diagram of the illustrative embodiment of the present invention, which is used in conjunction with person 100. The illustrative embodiment comprises master unit 101, ancillary unit 102-1, ancillary unit 102-2, cell phone 103, cellular telecommunications network 104, assistance monitoring facility 105, emergency medical services 106, local monitoring apparatus 107, and beacons 108-1, 108-2, and 108-3.

Master unit 101 is a wireless apparatus that:
continually receives measures of motion for person 100 from motion sensor 302-1 (shown in FIG. 3) in ancillary unit 102-1;
continually receives measures of motion for person 100 from motion sensor 302-2 (shown in FIG. 3) in ancillary unit 102-2;
continually receives measures of attitude from attitude sensor 202 (shown in FIG. 2);
continually receives measures of blood oxygen saturation level for person 100 from pulse oximeter 205 (shown in FIG. 2);
continually receives measures of ambient sound level from microphone 203 (shown in FIG. 2);
continually receives measures of ambient light level from light sensor 204 (shown in FIG. 2);
continually receives estimates of the location of person 100 from location finder 211 (shown in FIG. 2);
continually generates a motion profile for person 100 based on the measures of motion collected by ancillary unit 102-1 and ancillary unit 102-2;
continually generates estimates of the attitude of person 100 based on the measures of motion and the measures of attitude;
continually generates estimates of well-being of person 100 based on the measures of motion, the estimates of attitude, the measures of blood oxygen saturation level, the measures of ambient sound level, and the ambient light level;
continually generates estimates of whether person 100 needs assistance based on the estimates of well-being and signs of distress; and
when the estimate of whether person 100 needs assistance indicates that person 100 does need assistance, transmits a request for assistance for person 100.

The details of master unit 101, and the functions it performs, are described below and in the accompanying figures.

Ancillary unit 102-$i$, wherein $i \in \{1, 2\}$, are each a wireless apparatus that:
continually generates measures of motion for person 100 (with motion sensor 302-$i$ shown in FIG. 3);
continually transmits the measures of motion to master unit 101; and
vibrates (with tactile vibrator 303-$i$ shown in FIG. 3) under the direction of master unit 101.

The details of ancillary unit 102-$i$, and the functions it performs, are described below and in the accompanying figures.

A goal of the illustrative embodiment is to request assistance for person 100 when he or she does, in fact, need assistance and to refrain from requesting help for person 100 when he or she does not, in fact, need assistance. This implies that there are two types of errors that a personal assistance monitor can make.

First, the illustrative embodiment can estimate that person 100 needs assistance when, in fact, he or she does not. This is a "false positive" error. Second, the illustrative embodiment can estimate that person 100 does not need assistance when, in fact, he or she does. This is a "false negative" error. Both types of errors are undesirable.

A false positive error is a false alarm. If it occurs occasionally, it is generally not a problem, but if it occurs more often, it becomes a significant problem. A false negative error is like a fire alarm that is broken. If a fire occurs even once and the fire alarm does nothing, it is a significant problem. Therefore, the illustrative embodiment employs several mechanisms to reduce the occurrence of false positive errors and to eliminate the likelihood of false negative errors.

One way that the illustrative embodiment reduces the likelihood of false positive errors and false negative errors is to collect measures of motion at two locations on person 100's body. It will be clear to those skilled in the art however, after reading this disclosure, how to make and use alternative embodiments of the present invention that measure the motion of any number of locations on person 100's body (e.g., one location, three locations, four locations, five locations, six locations, eight locations, ten locations, twelve locations, etc.). In general, as the number of locations where measures of motion are collected increases, the likelihood of false positive and false negative errors decreases.

Another way that the illustrative embodiment reduces the likelihood of false positive errors and false negative errors is to collect measures of motion on two of person 100's limbs (i.e., an arm or a leg). For example, each measure of motion can be collected at any combination of the right upper arm, the left upper arm, the right elbow, the left elbow, the right forearm, the left forearm, the right wrist, the left wrist, the right hand, the left hand, any finger, the right thumb, the left thumb, the right index finger, the left index finger, the right middle finger, the left middle finger, the right ring finger, the left ring finger, the right pinky, the left pinky, each individual finger joint, the right thigh, the left thigh, the right knee, the left knee, the right lower leg, the left lower leg, the right ankle, the left ankle, the right foot, the left foot, each individual toe, and each individual toe joint. It will be clear to those skilled in the art, however, after reading this disclosure, how to make and use alternative embodiments of the present invention in which measures of motion are collected at a location that is not on a limb (e.g., on a person's head, neck, and/or trunk, etc.).

In accordance with the illustrative embodiment, measures of motion are collected at one location on person 100 by ancillary unit 102-1 and at a second location on person 100 by ancillary unit 102-2. Master unit 101, ancillary unit 102-1, and ancillary unit 102-2 are tangibly-distinct units and connected only via radio. It will be clear to those skilled in the art, however, after reading this disclosure, how to make and use alternative embodiments of the present invention in which one tangible unit collects measures of motion at two or more locations on person 100. Furthermore, it will be clear to those skilled in the art, after reading this disclosure, how to make and use alternative embodiments of the present invention that collect measures of motion at only one location on a person. In other words, some alternative embodiments of the present invention might avoid multiple units for any number of reasons (e.g., economics, personal comfort, ability of the embodiment to perform adequately without multiple units, etc.).

In accordance with the illustrative embodiment, person 100 is left-handed (i.e., left-hand dominant). The illustrative embodiment operates independently of hand (and foot) dominance, but it will be clear to those skilled in the art, after reading this disclosure, how to make and use alternative embodiments of the present invention that consider and take into account hand (and foot) dominance.

In accordance with the illustrative embodiment, ancillary unit 102-1 is affixed to the left wrist of person 100 so that all of the movements of the left wrist are transferred to and sensed by motion sensor 302-1 (shown in FIG. 3) in ancillary unit 102-1. Furthermore, ancillary unit 102-1 is affixed to the left wrist of person 100 so that motion sensor 302-1 is on the lunate bone (i.e., top of the left wrist bone). In accordance with the illustrative embodiment, ancillary unit 102-1 is configured as a bracelet. It will be clear to those skilled in the art, after reading this disclosure, how to make and use alternative embodiments of the present invention in which ancillary unit 102-1 is affixed to a different location on the person's body. Furthermore, it will be clear to those skilled in those skilled in the art how to make and use alternative embodiments of the present invention in which ancillary unit 102-1 has a different configuration and is affixed with a different method (e.g., an adhesive, subdermally, in clothing, etc.).

In accordance with the illustrative embodiment, ancillary unit 102-2 is affixed to the right wrist of person 100 so that all of the movements of the right wrist are transferred to and sensed by motion sensor 302-2 (shown in FIG. 3) in ancillary unit 102-2. Furthermore, ancillary unit 102-2 is affixed to the right wrist of person 100 so that motion sensor 302-2 is on the lunate bone (i.e., top of the right wrist bone). In accordance with the illustrative embodiment, ancillary unit 102-2 is configured as a bracelet. It will be clear to those skilled in the art, after reading this disclosure, how to make and use alternative embodiments of the present invention in which ancillary unit 102-2 is affixed to a different location on the person's body. Furthermore, it will be clear to those skilled in those skilled in the art how to make and use alternative embodiments of the present invention in which ancillary unit 102-2 has a different configuration and is affixed with a different method (e.g., an adhesive, subdermally, in clothing, etc.).

In accordance with the illustrative embodiment, master unit 101, ancillary unit 102-1, and ancillary unit 102-2 communicate via a low-power, energy-efficient radio protocol (e.g., ZigBee, Z-Wave, etc.), but it will be clear to those skilled in the art, after reading this disclosure, how to make and use alternative embodiments of the present invention in which master unit 101, ancillary unit 102-1, and ancillary unit 102-2 communicate via wireline.

Master unit 101, ancillary unit 102-1, and ancillary unit 102-2 are each waterproof and designed to be comfortable when worn by person 100 all of the time (i.e., when awake, when asleep, when showering, driving, watching television, doing the dishes, etc.). Master unit 101, ancillary unit 102-1, and ancillary unit 102-2 are to be worn all of the time because:

(i) they are not useful when they are not worn, and
(ii) the accuracy of the estimate of whether person 100 needs assistance is improved when they are worn all of the time.

Cell phone 103 is a wireless telecommunications device, as is well known to those skilled in the art and currently sold by companies such as Apple, Samsung, HTC, and others. Cell phone 103 comprises a Bluetooth® radio and is capable of being paired with master unit 101 in such a way that master unit 101 is capable of initiating and conducting voice and data communications to assistance monitoring facility 105 via cell phone 103 and network 104. It will be clear to those skilled in the art how to make and use cell phone 103.

Cellular telephone network 104 is a publicly-switched wireless telecommunications system as currently operated by companies such as AT&T Wireless, Verizon Wireless, and others. It will be clear to those skilled in the art how to make and use cellular telephone network 104.

Assistance monitoring facility 105 is a building that houses people and telecommunications equipment that:

(i) receives requests for assistance for person 100 from master unit 101,
(ii) deploys emergency medical services, when appropriate, and
(iii) transmits software updates to master unit 101.

Assistance monitoring facility 105 is described in detail below and in the accompanying figures.

Emergency medical services 106 are personnel and facilities that are dispatched by assistance monitoring facility 105 to the location of person 100. It will be clear to those skilled in the art how to make and use emergency medical services 106.

Local monitoring apparatus 107 is hardware and software that alerts people in the vicinity of person 100 when master unit 101 transmits a request for assistance for person 100. Local monitoring apparatus 107 is described in detail below and in the accompanying figures.

Beacons 108-1, 108-2, and 108-3 are low-power radio transmitters that are dispersed throughout an area where person 100 spends time. The radio signal from each of beacons 108-1, 108-2, and 108-3 is transmitted with a fixed power and is encoded so that they are distinguishable from each other. The purpose of beacons 108-1, 108-2, and 108-3 is to assist location finder 211 (shown in FIG. 2) in estimating the location of master unit 101. It will be clear to those skilled in the art, after reading this disclosure, how to make and use alternative embodiments of the present invention that employ any number of beacons.

The interaction of master unit 101, ancillary unit 102-1, ancillary unit 102-2, cell phone 103 cellular network 104, assistance monitoring facility 105, emergency medical services 106, local monitoring apparatus 107, and beacons 108-1, 108-2, and 108-3 is described in detail below and in the accompanying figures.

Figure 2:
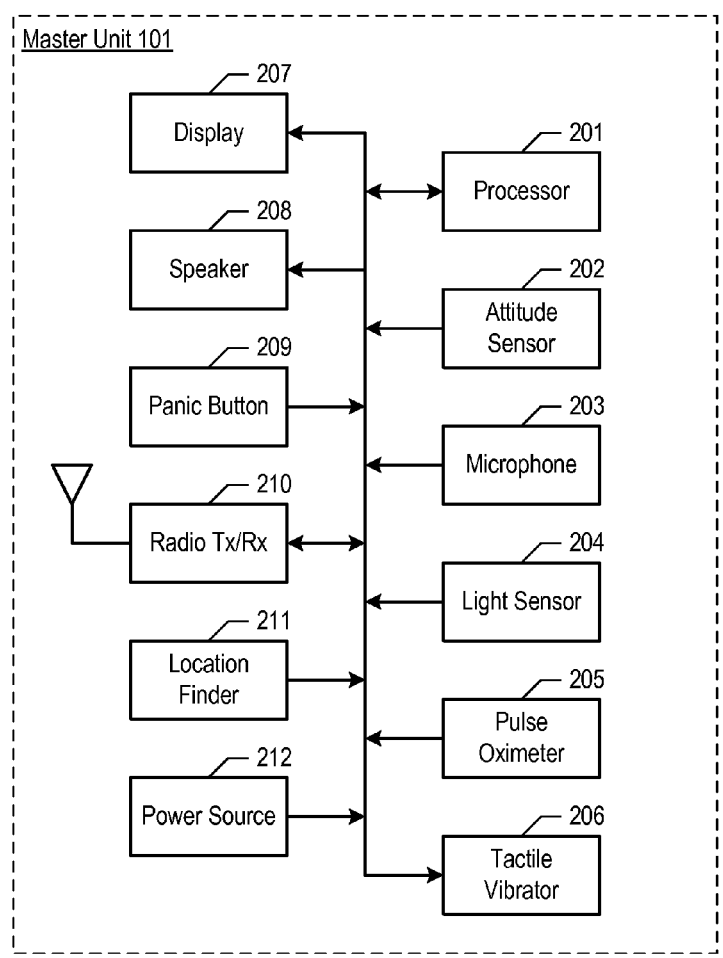
FIG. 2 depicts a block diagram of the salient components of master unit 101 in accordance with the illustrative embodiment.

FIG. 2 depicts a block diagram of the salient components of master unit 101 in accordance with the illustrative embodiment. Master unit 101 comprises: processor 201, attitude sensor 202, microphone 203, light sensor 204, pulse oximeter 205, tactile vibrator 206, display 207, speaker 208, panic button 209, radio transmitter and radio receiver 210, location finder 211, and power source 212, interconnected as shown.

Processor 201 comprises general-purpose programmable hardware, memory, a real-time clock, and software that enables master unit 101 to perform the functionality described in this disclosure. The real-time clock enables processor 201 to know the real time t, date, day of the week, month, and year at each moment. It will be clear to those skilled in the art, after reading this disclosure, how to make and use processor 201.

Attitude sensor 202 is a hardware input device that generates a three-dimensional measure of acceleration designated $\vec{\gamma}$, which can be sampled by processor 201. In accordance with the illustrative embodiment, attitude sensor 202 is a precision three-dimension micro-electro-mechanical systems accelerometer with 0.001 g resolution that directly measures acceleration. For example and without limitation, attitude sensor 202 is similar to the ADXL203 available from Analog Devices. In accordance with the illustrative embodiment, the measure of motion $\vec{Si}$ is a three-dimensional vector measure of acceleration, which comprises both magnitude and direction. The output of attitude sensor 202 is in units of $g=9.806$ meters/second$^2$.

The first purpose of attitude sensor 202 is to help the illustrative embodiment to ascertain the angular orientation or "attitude" of person 100 (i.e., if person 100 is upright, lying prone or supine, lying on his or her left or right side, etc.). Among other things, the attitude of person 100 is an indication of whether person 100 is sleeping or unwell, which when combined with other data is a factor in estimating the well-being of person 100.

Figure 3:
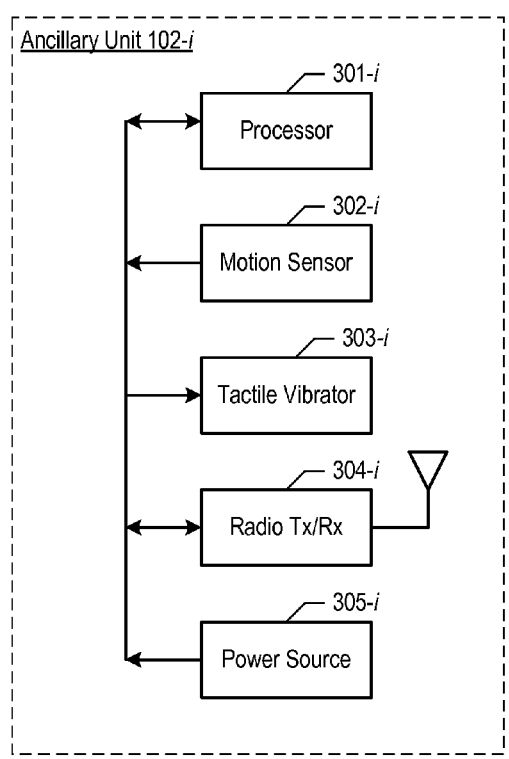
FIG. 3 depicts a block diagram of the salient components of ancillary unit 102-$i$, wherein i$\in\{1, 2\}$, in accordance with the illustrative embodiment.

The second purpose of attitude sensor 202 is to help some alternative embodiments of the present invention compensate for the disparity in the angular orientation of motion sensors 302-1 and 302-2 (which are shown in FIG. 3). This is described in detail below.

The third purpose of attitude sensor 202 is to generate additional measures of motion for a third location on person 100 for some alternative embodiments of the present invention.

The vector $\vec{\gamma}$ output from attitude sensor 202 is expressed in the coordinate system of attitude sensor 202, and, therefore, attitude sensor 202 is affixed to person 100 with a fixed angular orientation so that it is indicative of the attitude of person 100. It will be clear to those skilled in the art how to make and use attitude sensor 202.

Microphone 203 is hardware that converts the ambient sound level into an electrical signal that can be sampled by processor 201. Among other things, the ambient sound level in the vicinity of person 100 is a factor in estimating whether person 100 is sleeping and whether person 100 needs assistance or not. It will be clear to those skilled in the art how to make and use microphone 203.

Light sensor 204 is hardware that converts the ambient light level into an electrical signal that can be sampled by processor 201. Among other things, the ambient light level in the vicinity of person 100 is a factor in estimating whether person 100 is sleeping and whether person 100 needs assistance or not. It will be clear to those skilled in the art how to make and use light sensor 204.

Pulse oximeter 205 is hardware that continually detects the blood oxygen saturation level of person 100 and converts it into an electrical signal that can be sampled by processor 201. Among other things, the blood oxygen saturation level of person 100 is a factor in estimating whether person 100 needs assistance or not. It will be clear to those skilled in the art how to make and use pulse oximeter 205.

Tactile vibrator 206 is a hardware output device under the control of processor 201 that vibrates under the command of processor 201. In particular, processor 201 can control the intensity with which tactile vibrator 206 vibrates and the timing of when tactile vibrator 206 vibrates. For example, tactile vibrator is capable of vibrating:
  (1) below an intensity X,
  (2) above the intensity X and below an intensity Y, and
  (3) above the intensity Y,
wherein:
  (i) X and Y are real positive numbers,
  (ii) X is an intensity threshold above which person 100, while sleeping, is likely to elicit a response by, for example and without limitation, moving his or her body, and
  (iii) Y is an intensity threshold below which person 100 is unlikely to waken and above which person 100 is likely to waken.
It is well known to those skilled in the art how to make and control tactile vibrator 206.

Display 207 is a hardware output device under the control of processor 201 that provides:
  (i) a visual indication of the state of master unit 101,
  (ii) a programming interface to master unit 101, and
  (iii) a visual alert to person 100 that master unit 101 believes that person 100 needs assistance and is prompting person 100 to decline assistance.
It will be clear to those skilled in the art how to make and use display 207.

Speaker 208 is a hardware output device under the control of processor 201 that provides an acoustic output for master unit 101. Speaker 208 is used, for example and without limitation, to provide:
  (i) an audible alert to person 100 that master unit 101 believes that person 100 needs assistance and is prompting person 100 to decline assistance, and
  (ii) an audible (local) alarm that requests assistance for person 100 when person 100 fails to decline assistance, and
  (iii) an acoustic output for people or equipment at assistance monitoring facility 105 to speak to person 100.
It is well known to those skilled in the art how to make and use speaker 208.

Panic button 209 is a hardware input device that, when activated by person 100 or another person, directs processor 201 to transmit a request for assistance immediately. It is well known to those skilled in the art how to make and use panic button 209.

Radio 210 is a hardware output device that comprises a radio transmitter and a radio receiver that are capable of:
  (i) communicating with ancillary units 102-1 and 102-2 via a low-power, energy-efficient radio protocol to receive measures of motion from them, to direct ancillary units 102-1 and 102-2 to vibrate, and to provide programming updates to ancillary units 102-1 and 102-2,
  (ii) communicating via the Bluetooth® protocol with cell phone 103 to provide the functionality described in this disclosure, and
  (iii) communicating with local monitoring apparatus 107 via a low-power, energy-efficient radio protocol to provide the functionality described in this disclosure.
It will be clear to those skilled in the art how to make and use radio 210.

Location finder 211 is hardware and software for determining the location of master unit 101. In accordance with the illustrative embodiment, location finder 211 is a combination GPS receiver and RF Fingerprinting unit that is capable of resolving the location of master unit 101 to within 1 meter. To accomplish this, location finder 211 relies on the signals transmitted by beacons 108-1, 108-2, and 108-3.

Location finder 211 is useful in two distinct ways. First, when master unit 101 determines that person 100 needs assistance, location finder 211 enables master unit 101 to inform assistance monitoring facility 105 where person 100 is located. Second, the location of person 100 is helpful in estimating whether person 100 is asleep and whether person 100 needs assistance. For example, if person 100 is prone and in the kitchen, then it is more likely that person 100 needs assistance than when person 100 is prone in bed. For this reason, the location of person 100 is a factor in estimating whether person 100 needs assistance, as described below. It will be clear to those skilled in the art, after reading this disclosure, how to make and use alternative embodiments of the present invention that use other location technologies for locating master unit 101. In some alternative embodiments of the present invention, the output of location finder 211 is a one-bit indication of whether person 100 is in bed. It will be clear to those skilled in the art how to make and use location finder 211.

Power source 212 is an electrochemical battery and solar cell that supplies electrical energy to everything in master unit 101. It will be clear to those skilled in the art, after reading this disclosure, how to make and use alternative embodiments of the present invention in which power source 212 comprises other sources of energy, for example "kinetic capture" as in Rolex® Oyster® Perpetual watches, wireless power, etc. It will be clear to those skilled in the art how to make and use power source 212.

FIG. 3 depicts a block diagram of the salient components of ancillary unit 102-$i$, wherein i∈{1, 2}, in accordance with the illustrative embodiment. Ancillary unit 102-$i$ comprises: processor 301-$i$, motion sensor 302-$i$, vibrator 303-$i$, radio 304-$i$, and power source 305-$i$, interconnected as shown.

Processor 301-$i$ comprises general-purpose programmable hardware, memory, a real-time clock that is synchronized with the real-time clock in master unit 101, and software to enable ancillary unit 102-$i$ to perform the functionality described herein. It will be clear to those skilled in the art, after reading this disclosure, how to make and use processor 301-$i$.

Motion sensor 302-$i$ is a hardware input device that generates a three-dimensional measure of motion designated $\vec{Si}$, which can be sampled by processor 301-$i$. In accordance with the illustrative embodiment, motion sensor 302-$i$ is a precision three-dimension micro-electro-mechanical systems accelerometer with 0.001 g resolution that directly measures acceleration. For example and without limitation, motion sensor 302-$i$ is similar to the ADXL203 available from Analog Devices. In accordance with the illustrative embodiment, the measure of motion is a three-dimensional vector measure of acceleration that comprises both magnitude and direction. The output of motion sensor 302-$i$ is in units of g 9.806 meters/second$^2$.

It will be clear to those skilled in the art, after reading this disclosure, how to make and use alternative embodiments of the present invention in which motion sensor 302-$i$ directly measures acceleration in only one or two dimensions. In these embodiments, the measure of motion is a one- or two-dimensional vector measure of acceleration, respectively.

It will be clear to those skilled in the art, after reading this disclosure, how to make and use alternative embodiments of the present invention in which motion sensor 302-$i$ directly measures velocity (in one, two, or three dimensions). It will be clear to those skilled in the art that velocity can be directly measured in several ways. In these alternative embodiments, the direct measurements of velocity can be expressed and processed in terms of velocity or, alternatively, they can be converted into either estimates of acceleration or position with respect to time for processing.

It will be clear to those skilled in the art, after reading this disclosure, how to make and use alternative embodiments of the present invention in which motion sensor 302-$i$ directly measures position with respect to time (in one, two, or three dimensions). It will be clear to those skilled in the art that position can be directly measured in several ways. In these alternative embodiments, the direct measurements of position with respect to time can be expressed and processed in terms of position with respect to time or, alternatively, they can be converted into either estimates of acceleration or velocity for processing.

The measure of motion $\vec{St}$ output from motion sensor 302-$i$ is a three-dimensional vector that is expressed in the coordinate system of motion sensor 302-$i$. As motion sensor 302-$i$ rotates in space, its coordinate system also rotates (i.e., the coordinate system is fixed relative to the motion sensor). The measure of motion output from motion sensor 302-$i$ is denoted and is expressed in the coordinate system of motion sensor 302-$i$.

Tactile vibrator 303-$i$ is a hardware output device that vibrates under the direction of processor 301-$i$. In particular, processor 301-$i$ can control the intensity with which tactile vibrator 303-$i$ vibrates and the timing of when tactile vibrator 303-$i$ vibrates. For example, tactile vibrator is capable of vibrating:

(1) below an intensity X,
(2) above the intensity X and below an intensity Y, and
(3) above the intensity Y, wherein:
(i) X and Y are real positive numbers,
(ii) X is an intensity threshold above which person 100, while sleeping, is likely to elicit a response by, for example and without limitation, moving his or her body, and
(iii) Y is an intensity threshold below which person 100 is unlikely to waken and above which person 100 is likely to waken.

It is well known to those skilled in the art how to make and control tactile vibrator 303-$i$.

Radio 304-$i$ is a hardware output device that comprises a radio transmitter and radio receiver that is capable of transmitting measures of motion to master unit 101, receiving instructions from master unit 101, and performing the function described in this disclosure. It will be clear to those skilled in the art, after reading this disclosure, how to make and use alternative embodiments of the present invention in which ancillary unit 102-$i$ communicate with master unit 101 through acoustic signaling and/or free-space optical signaling rather than radio. It will be clear to those skilled in the art how to make and use radio 304-$i$.

Power source 305-$i$ is identical to power source 212 and provides electrical energy to everything in ancillary unit 102-$i$. It will be clear to those skilled in the art how to make and use power source 305-$i$.

Figure 4:
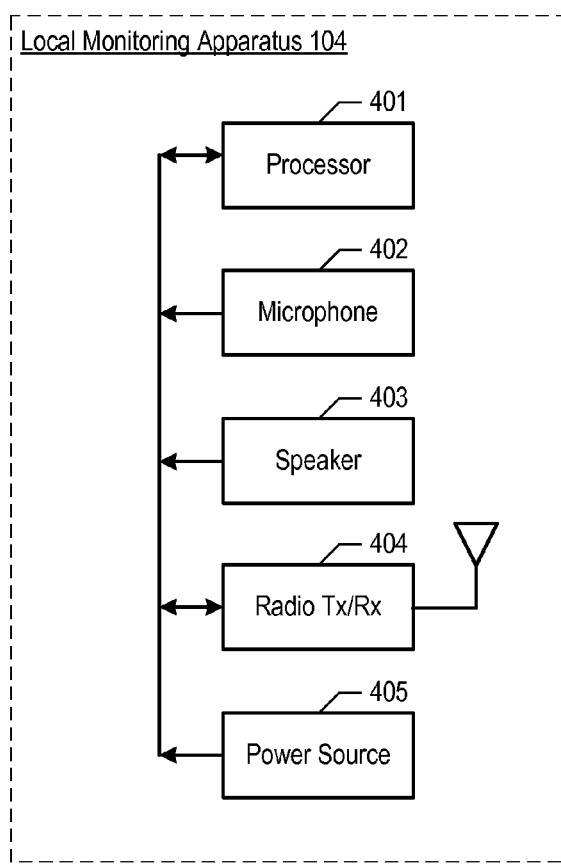
FIG. 4 depicts a block diagram of the salient components of local monitoring apparatus 104, in accordance with the illustrative embodiment of the present invention.

FIG. 4 depicts a block diagram of the salient components of local monitoring apparatus 104, in accordance with the illustrative embodiment of the present invention. Local monitoring apparatus comprises processor 401, microphone 402, speaker 403, radio 404, and power source 405, interconnected as shown.

Processor 401 comprises general-purpose programmable hardware, memory, a real-time clock that is synchronized with the real-time clock in master unit 101, and software to enable local monitoring apparatus 104 to perform the functionality described herein. It will be clear to those skilled in the art, after reading this disclosure, how to make and use processor 401.

Microphone 402 is a hardware input device that converts sound into an electrical signal that can be sampled by processor 401. Among other things, the ambient sound level in the vicinity of person 100 is a factor in estimating whether person 100 needs assistance or not. Furthermore, microphone 402 enables person 100 to speak to assistance monitoring facility 105. It will be clear to those skilled in the art how to make and use microphone 402.

Speaker 403 is a hardware output device under the control of processor 401 that provides an acoustic output for local monitoring unit 104. Speaker 403 is used, for example and without limitation, to provide:
  (i) an audible alert to person 100 that master unit 101 believes that person 100 needs assistance and is prompting person 100 to decline assistance, and
  (ii) an audible (local) alarm that requests assistance for person 100 when person 100 fails to decline assistance, and
  (iii) an acoustic output for people or equipment at assistance monitoring facility 105 to speak to person 100.
It is well known to those skilled in the art how to make and use speaker 403.

Radio 404 comprises a radio transmitter and a radio receiver that are capable of communicating with master unit 101 to provide the functionality described in this disclosure. It will be clear to those skilled in the art how to make and use radio 404.

Power source 406 is a wire line power source that is plugged into a 60 Hz wall plug. It will be clear to those skilled in the art how to make and use power source 406.

Figure 5:
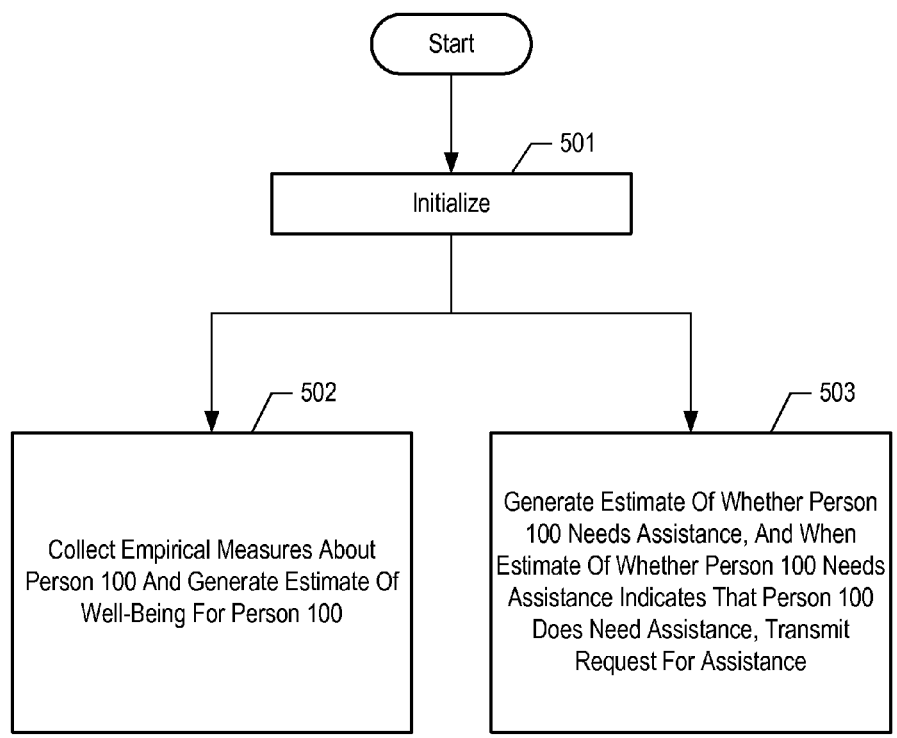
FIG. 5 depicts a flowchart of the salient tasks performed by the illustrative embodiment of the present invention.

FIG. 5 depicts a flowchart of the salient tasks performed by the illustrative embodiment of the present invention.

At task 501, master unit 101, ancillary unit 102-1, ancillary unit 102-2, cell phone 103, assistance monitoring facility 105, and local monitoring apparatus 107 are initialized. Task 501 is described in detail below and in the accompanying figure.

At task 502, processor 201 in master unit 101 collects empirical measures about person 100 and generates an estimate of well-being for person 100. For example and without limitation, processor 201:
  (1) continually receives a temporal series of measures of motion from motion sensor 302-1 (e.g., $\vec{S1(c-1)}, \vec{S1(c)}, \vec{S1(c+1)}$, etc.);
  (2) continually receives a temporal series of measures of motion from motion sensor 302-2 (e.g., $\vec{S2(c-1)}, \vec{S2(c)}, \vec{S2(c+1)}$, etc.);
  (3) continually receives a temporal series of measure of attitude of person 100 from attitude sensor 202 (e.g., $\vec{\gamma(c-1)}, \vec{\gamma(c)}, \vec{\gamma(c+1)}$, etc.);
  (4) continually receives a temporal series of measures of ambient sound level from microphone 203 (e.g., $\beta(c-1), \beta(c), \beta(c+1)$, etc.);
  (5) continually receives a temporal series of measures of ambient light level from light sensor 204 (e.g., $\delta(c-1), \delta(c), \delta(c+1)$, etc.);
  (6) continually receives a temporal series of measures of blood oxygen saturation level of person 100 from pulse oximeter 205 (e.g., $\phi(c-1), \phi(c), \phi(c+1)$, etc.);
  (7) continually receives a temporal series of estimates of the location of master unit 101 from location finder 211 (e.g., $\omega(c-1), \omega(c), \omega(c+1)$, etc.);
  (8) continually generates estimates of the attitude of person 100 based on the measures of motion and the measures of attitude;
  (9) continually generates estimates of well-being of person 100 based on the measures of motion, the estimates of attitude, the measures of blood oxygen saturation level, the measures of ambient sound level, and the ambient light level;
  (10) continually generates estimates of whether person 100 needs assistance based on the estimates of well-being and signs of distress; and
  (11) when the estimate of whether person 100 needs assistance indicates that person 100 does need assistance, transmits a request for assistance for person 100.

In particular, processor 201 samples attitude sensor 202, microphone 203, light sensor 204, pulse oximeter 205, and location finder 211 every 10 seconds. It will be clear to those skilled in the art, after reading this disclosure, how to make and use alternative embodiments of the present invention in which each of these are sampled at a different rate.

Furthermore, processor 301-$i$, wherein $i \in \{1, 2\}$, samples motion sensor 302-$i$ every 40 milliseconds, which yields 25 measures of motion $\vec{St}$ per second. Ancillary unit 102-$i$ then transmits the measures of motion $\vec{St}$ to master unit 101 for analysis.

In accordance with the illustrative embodiment, ancillary unit 102-1 and ancillary unit 102-2 each generate a measure of motion at a constant 25 samples per second. A sampling rate of 25 samples per second gleans most of the useful motion data regarding the well-being of person 100 and yet generates a manageable amount of data for today's inexpensive microprocessors and microcontrollers. It will be clear to those skilled in the art, however, after reading this disclosure, how to make and use alternative embodiments of the present invention that sample at:
  (i) a higher constant rate (e.g., 40 samples per second, 60 samples per second, 100 samples per second, etc.),
  (ii) a lower constant rate (e.g., 12.5 samples per second, 6 samples per second, 1 sample per second, etc.), or
  (iii) a variable rate (e.g., a slow sampling rate when the measure of motion is changing less rapidly and a higher sampling rate when the measure of motion is changing more rapidly, etc.).
It will be clear to those skilled in the art, after reading this disclosure, that a higher sampling rate might glean more useful information but increases the amount of data that must be stored and analyzed. In contrast, a lower sampling rate might, in some cases, miss useful information but decreases the amount of data that must be stored and analyzed. A variable sampling rate can capture most of the useful information without extraneous data but might complicate the programming of master unit 101. Task 502 is performed continually and concurrently with task 503. Task 502 is described in detail below and in the accompanying figures.

At task 503, processor 201:
 (i) generates an estimate of whether person 100 needs assistance, and
 (ii) when the estimate of whether person 100 needs assistance indicates that person 100 does need assistance, transmits a request for assistance for person 100.

Task 502 is performed continually and concurrently with task 503. Task 503 is described in detail below and in the accompanying figures.

Figure 6:
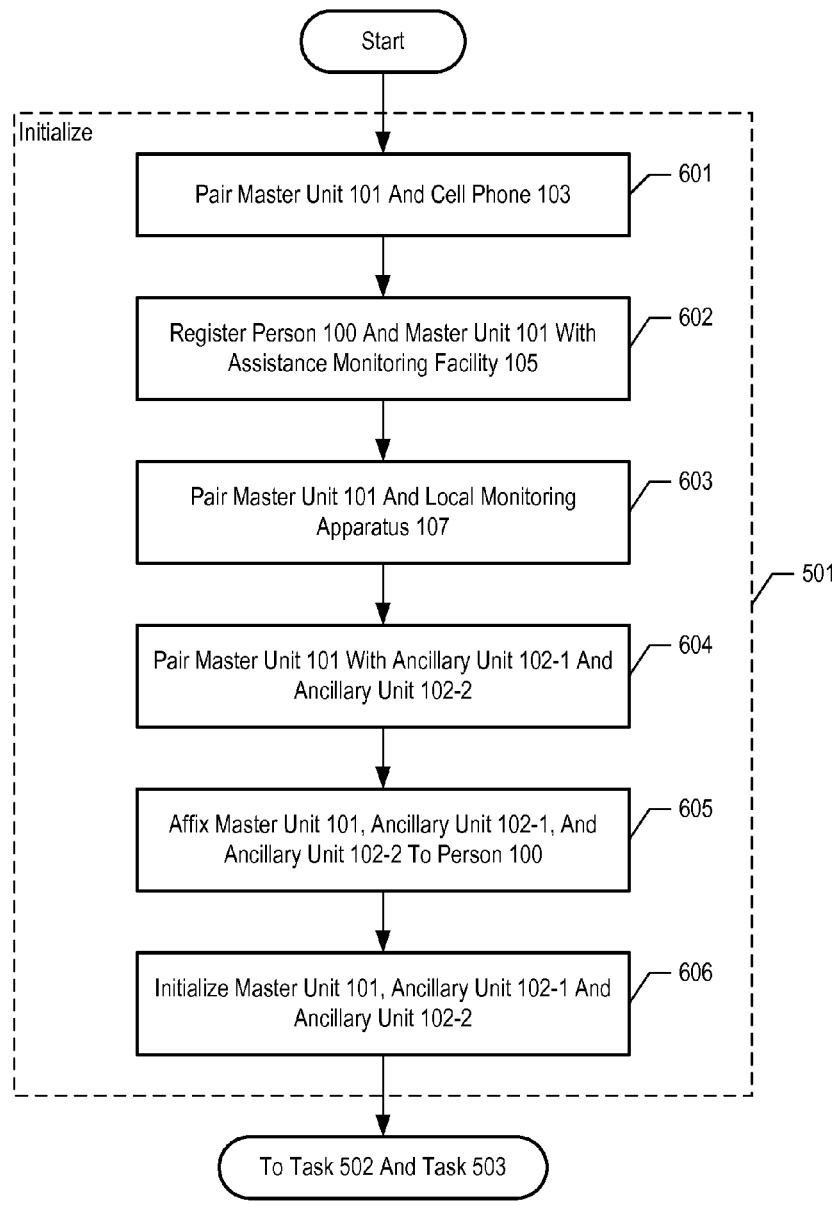
FIG. 6 depicts a flowchart of the salient tasks performed by the illustrative embodiment in task 501—initializing master unit 101, ancillary unit 102-1, ancillary unit 102-2, cell phone 103, assistance monitoring facility 105, and local monitoring apparatus 107.

FIG. 6 depicts a flowchart of the salient tasks performed by the illustrative embodiment in task 501—initializing master unit 101, ancillary unit 102-1, ancillary unit 102-2, cell phone 103, assistance monitoring facility 105, and local monitoring apparatus 107.

At task 601, master unit 101 is paired with cell phone 103 via the Bluetooth® protocol so that master unit 101 can use cell phone 103:
 to transmit a request for assistance for person 100,
 to transmit the location of person 100.
 to transmit information (e.g., the estimate of well-being of person 100, the motion profile, etc.) regarding the well-being of person 100 to assistance monitoring facility 105,
 to receive data and programming updates from assistance monitoring facility 105, and
 to enable voice communications between assistance monitoring facility 105 and person 100.

It will be clear to those skilled in the art, after reading this disclosure, how to perform task 601.

At task 602, person 100 and master unit 101 are registered with assistance monitoring facility 105 so that assistance monitoring facility 105 associates person 100 with cell phone 103 and telemetry from master unit 101. It will be clear to those skilled in the art, after reading this disclosure, how to perform task 602.

At task 603, master unit 101 is paired with local monitoring apparatus 107 via a low-power, energy-efficient radio protocol (e.g., ZigBee, Z-Wave, etc.). Master unit 101 is paired with local monitoring apparatus 107 so that master unit 101 can:
 (i) trigger, when appropriate, visual and audible alarms in local monitoring apparatus 107 to request assistance for person 100, and
 (ii) trigger, when appropriate, a visual and audible stimulus that prompts person 100 to decline assistance.

It will be clear to those skilled in the art, after reading this disclosure, how to perform task 603.

At task 604, master unit 101 is paired with ancillary unit 102-1 and ancillary unit 102-2 so that:
 ancillary unit 102-$i$ can transmit and master unit 101 can receive the measures of motion $\vec{S}t_i$,
 master unit 101 can transmit and ancillary unit 102-$i$ can receive a direction to vibrate tacitile vibrator 303-$i$, and
 master unit 101 can transmit and ancillary unit 102-$i$ can receive other instructions, data, and software updates.

It will be clear to those skilled in the art, after reading this disclosure, how to perform task 604.

At task 605, ancillary unit 102-1 is firmly affixed to a first location on person 100 so that there is little independent motion of ancillary unit 102-1 with respect to the first location. Furthermore, ancillary unit 102-2 is firmly affixed to a second location on person 100 so that there is little independent motion of ancillary unit 102-2 with respect to the second location. Ancillary unit 102-1 and ancillary unit 102-1 should be affixed to person 100 so that they are comfortable but also so that the vast majority of the motion of person 100 at their location causes the units to move accordingly.

Master unit 101 is firmly affixed to a third location on person 100 so that there is little independent motion of master unit 101 with respect to the third location. In accordance with the illustrative embodiment, master unit 101 has an angular orientation (because attitude sensor 202 shown in FIG. 2 has an angular orientation). Therefore, master unit 101 is affixed to person 100 so that the angular orientation of person 100's trunk is transferred to, and can be detected by, attitude sensor 202. Master unit 101 should be affixed to person 100 so that it is comfortable but also so that the angular orientation of the person at the third location is detected by master unit 101.

In accordance with the illustrative embodiment, ancillary unit 102-1 is affixed to the left wrist of person 100, ancillary unit 102-2 is affixed to the right wrist of person 100, and master unit 101 is affixed to the chest of person 100 at the upper sternum (as shown in FIG. 1).

In accordance with the illustrative embodiment of the present invention, ancillary unit 102-1 and ancillary unit 102-2 are on opposite sides of the mid-Sagittal plane. This is advantageous because some ailments and indications of well-being (e.g., strokes, some tremors, etc.) are easier to diagnose when measures of motion are made on opposites sides of the mid-Sagittal plane. In contrast, in some alternative embodiments of the present invention, ancillary unit 102-1 and ancillary unit 102-2 are on the same side of the mid-Sagittal plane (e.g., ancillary unit 102-1 on the right wrist and ancillary unit 102-2 on the right ankle, ancillary unit 102-1 on the left wrist and ancillary unit 102-2 on the left ankle, etc.).

In accordance with the illustrative embodiment of the present invention, ancillary unit 102-1 and ancillary unit 102-2 are on the same side of the transverse plane. In contrast, in some other embodiments of the present invention, ancillary unit 102-1 and ancillary unit 102-2 might be on opposite sides of the transverse plane (e.g., ancillary unit 102-1 on the right wrist and ancillary unit 102-1 on the left ankle, ancillary unit 102-1 on the right ankle and ancillary unit 102-1 on the left wrist, etc.), which can be advantageous for diagnosing some ailments (e.g., nocturnal leg cramps, etc.).

In some alternative embodiments of the present invention, one or both of the ancillary unit 102-1 and ancillary unit 102-2 are on the head of person 100. In some alternative embodiments of the present invention, one or both of the ancillary unit 102-1 and ancillary unit 102-2 are on the same limb of person 100. Whenever ancillary unit 102-1 or ancillary unit 102-2 are affixed or re-affixed on person 100 (e.g., moved from a wrist to an ankle, etc.), task 506 must be performed.

In accordance with the illustrative embodiment, master unit 101 is located on the mid-Sagittal plane, but it will be clear to those skilled in the art, after reading this disclosure, how to make and use alternative embodiments of the present invention in which master unit 101 is located elsewhere on person 101 (e.g., the back, the neck, the head, etc.).

At task 606, master unit 101, ancillary unit 102-1, and ancillary unit 102-2 are initialized. As part of task 606, several parameters are reset. In particular,
 (i) the first threshold of well-being parameter $T_1$ is set to 0.001,
 (ii) the second threshold of well-being parameter $T_2$ is set to 0.003,
 (iii) the third threshold of well-being parameter $T_3$ is set to 0.005,
 (iv) the value of parameter B, which is associated with the second pattern of distress, is set to 0.002, and
 (v) a counter c is initialized to zero.

It will be clear to those skilled in the art, after reading this disclosure, how to perform task 606. It will further be appreciated by those skilled in the art that some other embodiments of the present invention might employ different initial threshold values for one or more of parameters B, $T_1$, $T_2$, and $T_3$ (e.g., based on whether person 100 is known to move very little in his or her sleep, etc.), and it will be clear to those skilled in the art, after reading this disclosure, how to make and use such alternative embodiments.

Figure 7:
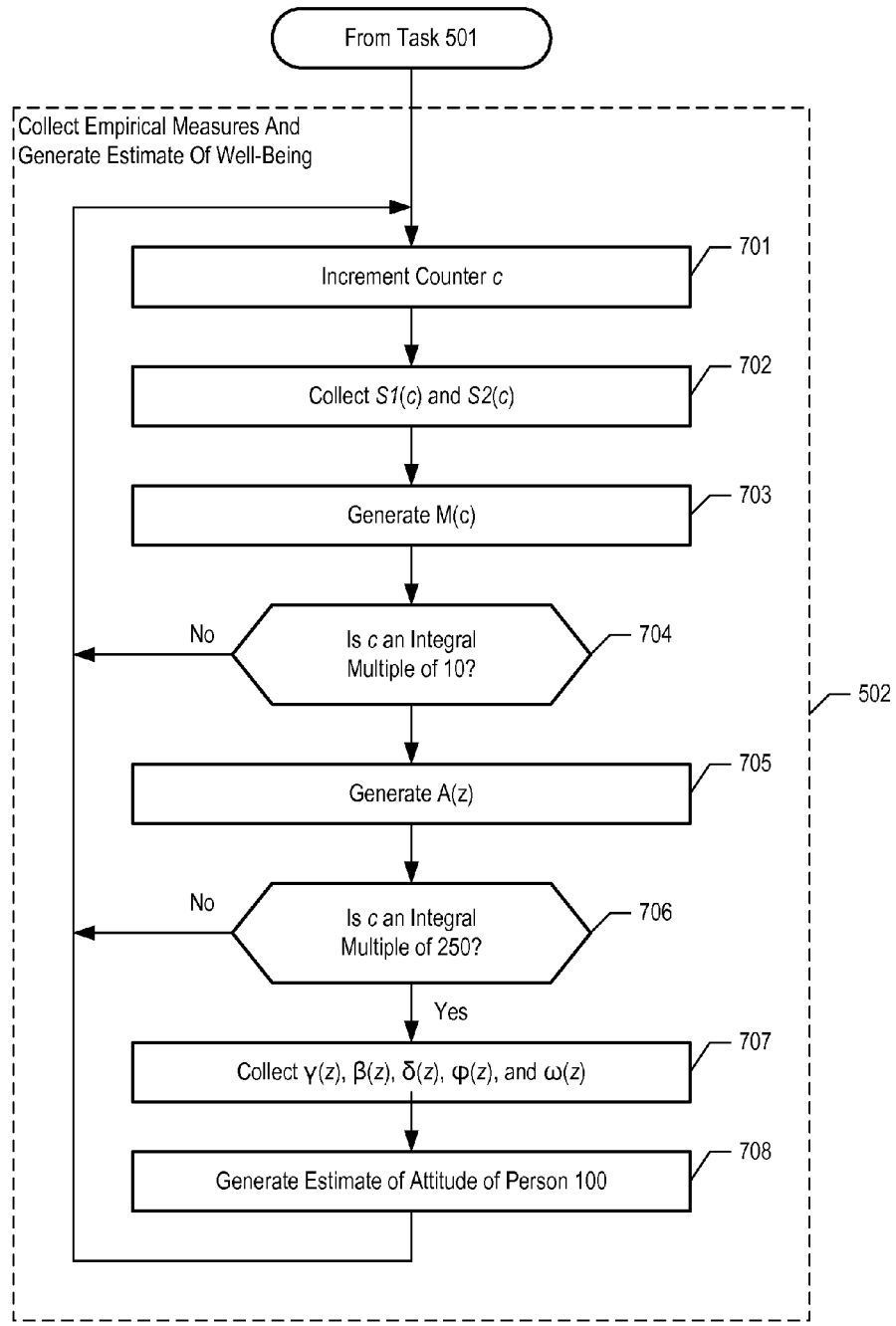
FIG. 7 depicts a flowchart of the salient tasks performed by the illustrative embodiment in task 502—collect measures of motion for person 100 and generate the motion profile.

FIG. 7 depicts a flowchart of the salient tasks performed by the illustrative embodiment in task 502—collect empirical measures for person 100 and generate the estimate of well-being.

At task 701, processor 201 increments the counter c by one.

At task 702, processor 201:

(i) receives a measure of motion $\overrightarrow{S1(c)}$ from motion sensor 302-1, and (ii) receives a measure of motion $\overrightarrow{S2(c)}$ from motion sensor 302-2.

At task 703, processor 201 generates a scalar value M(c), which equals:

$$M(c) = abs(\|(\overrightarrow{S1(c)} - \overrightarrow{S1(c-1)}) - (\overrightarrow{S2(c)} - \overrightarrow{S2(c-1)})\|) \quad \text{(Eq. 1)}$$

wherein $abs(\|\vec{x}\|)$ is the absolute value of the magnitude portion of the vector x. The inventors have recognized that M(c) is convenient for two reasons. First, M(c) is a scalar and is computationally easier to work with than $\overrightarrow{S1(c)}$ and $\overrightarrow{S2(c)}$, which are vectors, and yet M(c) reflects both translational and rotational motion in both $\overrightarrow{S1}$ and $\overrightarrow{S2}$. Second, the formula for M(c) is designed so that values of M(c) emphasize motion caused by person 100's muscles and de-emphasize motion caused by external forces. This is important because the inventors recognized that the movement due to an external force on person 100 is substantially reflected throughout person 100 while the movement due to a muscle is substantially isolated to the location near the muscle. For example, when a person rides in an accelerating elevator, the same acceleration is detectable everywhere on the person. But when a man scratches his nose with his right hand on the accelerating elevator, the acceleration due to the muscles of the right hand is substantially confined to the right arm and substantially absent in the left hand. The question then arises, how can the acceleration from the elevator be distinguished from the acceleration of the muscles of the right hand?

The answer—the inventors recognized—is that the motion due to person 100's muscles can be substantially isolated from the motion on person 100 due to external forces by:

(i) simultaneously collecting measures of motion at two locations that are substantially muscularly independent (e.g., the two wrists, an ankle and a wrist, etc.), and (ii) computing the difference between the simultaneously-collected measures of motion.

Because external forces are reflected equally in both $\overrightarrow{S1}$ and $\overrightarrow{S2}$, their difference is substantially free of the effects of external forces and yet reflects the motion due to muscular movement. As will be appreciated by those skilled in the art, in some other embodiments of the present invention information from vectors $\overrightarrow{S1(c)}$ and $\overrightarrow{S2(c)}$ might be combined in some alternative fashion, rather than by computing a vector difference, and it will be clear to those skilled in the art, after reading this disclosure, how to make and use such alternative embodiments. Furthermore, it will be clear to those skilled in the art, after reading this disclosure, how to make and use alternative embodiments that use more than two sensors and in which multiple pair-wise differences are computed between some or all of the individual measures of motion.

At task 704, processor 201 determines if c is an integral multiple of 10 (e.g., 10, 20, 30, etc.). If it is, then control proceeds to task 705; otherwise control proceeds to task 701.

At task 705, processor generates the value A(z), where:

$$z = c/10 \quad \text{(Eq. 2)}$$

$$A(z) = \frac{1}{10} \sum_{i=0}^{9} M(c-i) \quad \text{(Eq. 3)}$$

The value A(z) is an average of M(c) for the last 400 milliseconds or 10 values of M(c). Upon the completion of 705, a new motion profile is generated, which comprises:

(i) the most recent 120 seconds of the measures of motion, which is $\overrightarrow{S1(c-2999)}$ through $\overrightarrow{S1(c)}$, (ii) the most recent 120 seconds of the measures of motion, which is $\overrightarrow{S2(c-2999)}$ through $\overrightarrow{S2(c)}$, (iii) the most recent 120 seconds of the values of M( ), which is M(c-2999) through M(c), and (iv) the most recent 30 minutes of the values of A( ), which is A(z-4499) through A(z).

It will clear to those skilled in the art, after reading this disclosure, how to make and use alternative embodiments of the present invention in which the motion profile has a different composition.

At task 706, processor 201 determines if c is a multiple of 250 (e.g., 250, 500, 750, etc.). If it is, then control proceeds to task 707; otherwise control proceeds to task 701.

At task 707, processor 201:

(i) receives a measure of attitude $\overrightarrow{\gamma(z)}$ of person 100 from attitude sensor 202, (ii) receives a measure of ambient sound level β(z) from microphone 203, (iii) receives a measure of ambient light level δ(z) from light sensor 204, (iv) receives a measure of blood oxygen saturation level φ(z) of person 100 from pulse oximeter 205, and (v) receives an estimate of the location of master unit 101 ω(z) from location finder 211.

At task 708, processor 201 generates an estimate of the attitude of person 100 $\overrightarrow{\alpha(z)}$ based on:

(i) the measure of motion $\overrightarrow{S1(c)}$, which in accordance with the illustrative embodiment is a three-dimensional measure of acceleration, (ii) the measure of motion $\overrightarrow{S2(c)}$, which in accordance with the illustrative embodiment is a three-dimensional measure of accelerations, and (iii) the measure of attitude $\overrightarrow{\gamma(z)}$, which in accordance with the illustrative embodiment is a three-dimensional measure of acceleration.

In accordance with the illustrative embodiment, the estimate of the attitude of person 100 equals:

$$\overrightarrow{\alpha(z)} = \overrightarrow{\gamma(z)} + \frac{\overrightarrow{S1(c)} + \overrightarrow{S2(c)}}{4} \quad \text{(Eq. 4)}$$

It will be clear to those skilled in the art, after reading this disclosure, how to make and use alternative embodiments of the present invention that generate the estimate of the attitude of person 100 in accordance with another formula. For example, in embodiments of the present invention that do not comprise attitude sensor 202, the estimate of the attitude of person 100 would not comprise a value for $\vec{\gamma(z)}$.

On the completion of task 708, a new estimate of the well-being of person 100 is generated, which comprises:
 (i) the motion profile,
 (ii) the most recent value of the estimate of attitude $\vec{a\alpha(z)}$.
 (iii) the most recent measure of ambient sound level $\beta(z)$ from microphone 203,
 (iii) the most recent measure of ambient light level $\delta(z)$ from light sensor 204,
 (iv) the most recent measure of blood oxygen saturation level $\phi(z)$ of person 100 from pulse oximeter 205, and
 (v) the most recent estimate of the location of master unit 101 $\omega(z)$ from location finder 211.

It will clear to those skilled in the art, after reading this disclosure, how to make and use alternative embodiments of the present invention in which the estimate of well-being has a different composition.

Figure 8:
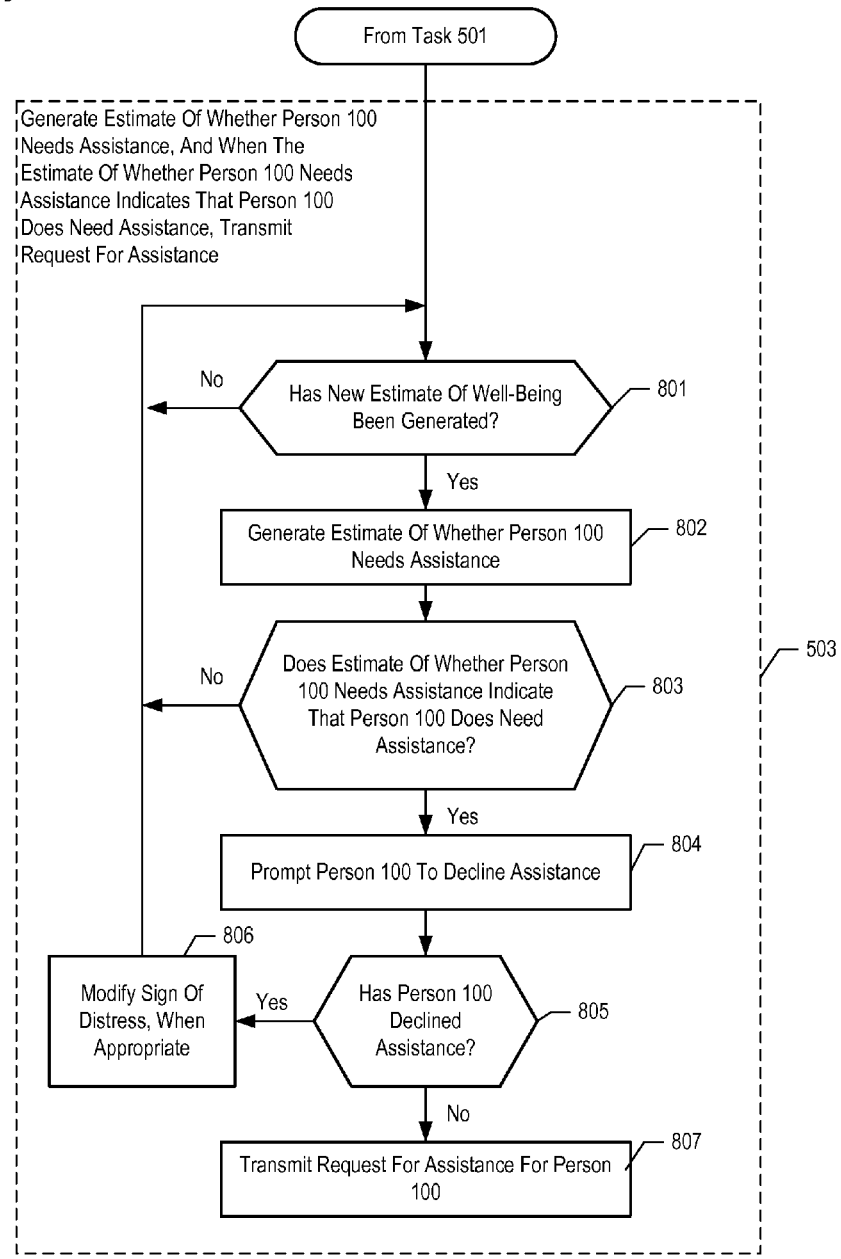
FIG. 8 depicts a flowchart of the salient tasks performed by the illustrative embodiment in task 503—generating an estimate of whether person 100 needs assistance, when the estimate of whether person 100 needs assistance indicates that person 100 does need assistance, transmitting a request for assistance.

FIG. 8 depicts a flowchart of the salient tasks performed by the illustrative embodiment in task 503—generating an estimate of whether person 100 needs assistance, and when the estimate of whether person 100 needs assistance indicates that person 100 does need assistance, transmitting a request for assistance.

At task 801, processor 201 determines if a new estimate of well-being has been generated (i.e., has task 708 has been performed). If it has, control proceeds to task 802; otherwise control proceeds back to task 801. In accordance with the illustrative embodiment, task 802 is performed after each time that task 708 is performed, but it will be clear to those skilled in the art, after reading this disclosure, how to make and use alternative embodiments of the present invention in which it is performed at a different time.

At task 802, processor 201 generates an estimate of whether person 100 needs assistance. Task 802 is described in detail below and in the accompanying figures.

At task 803, processor 201 determines if the estimate of whether person 100 needs assistance indicates that person 100 does need assistance. In accordance with the illustrative embodiment, this is accomplished by determining if the value of E—the estimate of whether person 100 needs assistance—generated in task 802 equals or exceeds ten (10). It will be clear to those skilled in the art, after reading this disclosure, how to make and use alternative embodiments of the present invention that determines if the estimate of whether person 100 needs assistance indicates that person 100 does need assistance in another way. When processor 201 determines that the estimate of whether person 100 needs assistance indicates that person 100 does need assistance, control passes to task 804; otherwise control passes to task 801.

At task 804, processor 201 prompts person 100 to decline assistance. The purpose of task 804 is to prevent master unit 101 from transmitting a request for assistance for person 100, when, in fact, assistance is not needed (i.e., committing a false positive error). In other words, just because processor 201 determined in task 803 that the estimate of whether person 100 needs assistance indicates that person 100 does need assistance does not guarantee that it is correct. Therefore, task 804 serves as a check to prevent the illustrative embodiment from committing a false positive error. Task 804 is described in detail below and in the accompanying figures.

At task 805, processor 201 affects control based on whether person 100 has declined assistance in task 804. When processor 201 determines that person 100 has declined assistance, control proceeds to task 806; otherwise, control proceeds to task 807.

At task 806, processor 201 modifies the criteria used to evaluate the estimate of well-being (e.g., the sign(s) of distress observed in the motion profile, etc.) in task 803 based on the fact that it yielded a false positive error. By modifying the criteria used to evaluate the estimate of well-being that yielded the false positive error, the likelihood of future false positive errors is reduced. Task 806 is described in detail below and in the accompanying figures.

At task 807, processor 201 transmits a request for assistance for person 100. Task 807 is described in detail below and in the accompanying figures.

Figure 9:
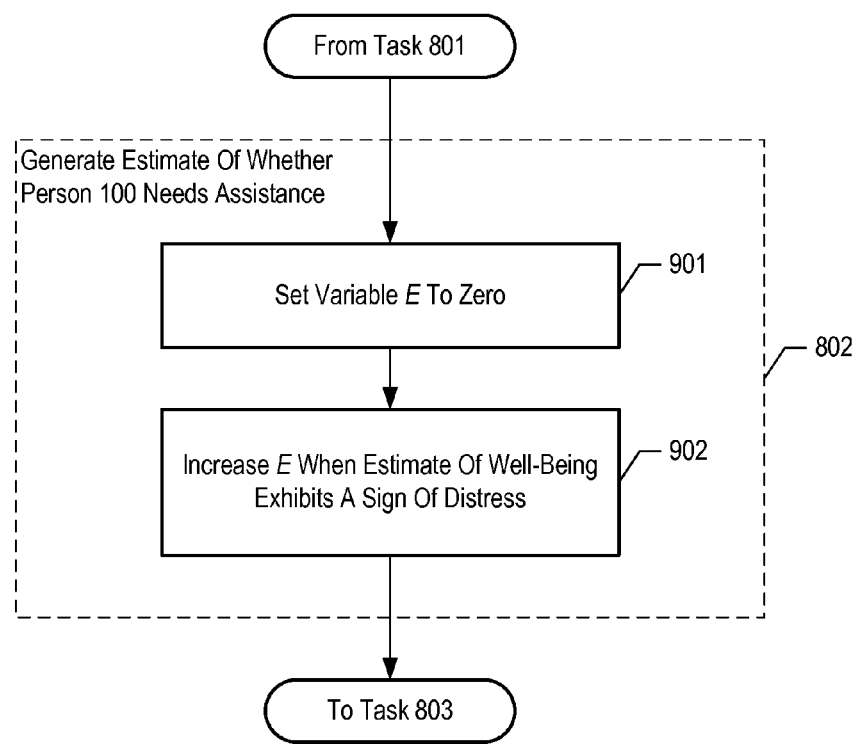
FIG. 9 depicts a flowchart of the salient tasks performed by processor 201 in task 802—generating an estimate of whether person 100 needs assistance.

FIG. 9 depicts a flowchart of the salient tasks performed by processor 201 in task 802—generating an estimate of whether person 100 needs assistance.

At task 901, processor 201 sets a parameter E to zero. At the end of task 802, the parameter E is a scalar that represents the estimate of whether person 100 needs assistance.

At task 902, processor increases the value of the parameter E when the estimate of well-being exhibits a sign of distress. In accordance with the illustrative embodiment, there are two distinct signs of distress:
 (i) patterns of distress, and
 (ii) failures to reach a threshold of well-being.

The first sign of distress—a pattern of distress—is a pattern in the estimate of well-being that suggests that person 100 is in need of assistance. Some patterns of distress are periodic and detect, for example and without limitation, tremors, shuddering, shivering, etc. Some patterns of distress are not periodic and detect, for example and without limitation, falls, etc. The illustrative embodiment tests for both periodic and non-periodic patterns of distress.

The second sign of distress—a failure of the estimate of well-being to reach a threshold of well-being—is self explanatory. This is based on the recognition that a person who is not in need of assistance, even when asleep, will exhibit some level of a trait (e.g., some minimum level of motion, some minimum blood oxygen saturation level, etc.). Therefore, each threshold of well-being is the minimum level of a trait, such as motion or blood oxygenation saturation level, that is acceptable without suggesting that person 100 is in distress.

To reduce the likelihood of both false-positive errors and false-negative errors, some of the signs of distress are characterized by one or more parameters. The illustrative embodiment adaptively modifies the parameters based on time, past estimates of well-being, and occurrences of person 100 declining assistance in task 805.

Task 902 is described in detail below and in the accompanying figures.

Figure 10:
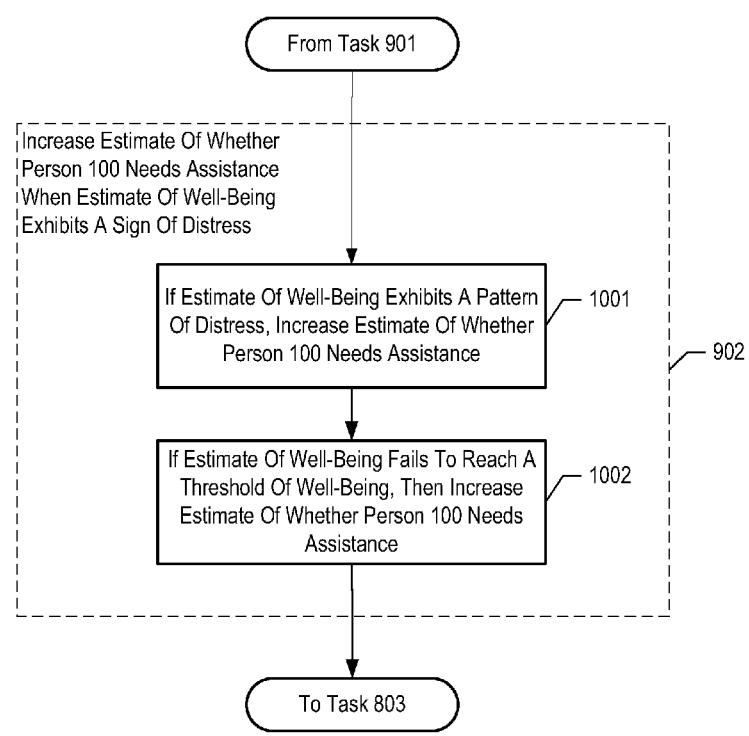
FIG. 10 depicts a flowchart of the salient tasks performed by processor 201 in task 902—increasing the parameter E—the estimate of whether person 100 needs assistance.

FIG. 10 depicts a flowchart of the salient tasks performed by processor 201 in task 902—increasing the parameter E—the estimate of whether person 100 needs assistance—when the estimate of well-being exhibits a sign of distress.

At task 1001, processor 201 determines whether the estimate of well-being exhibits a sign of distress by exhibiting a pattern of distress. Task 1001 is described in detail below and in the accompanying figures.

At task 1002, processor 201 determines whether the estimate of well-being exhibits a sign of distress by failing to reach a threshold of well-being. Task 1002 is described in detail below and in the accompanying figures.

Figure 11:
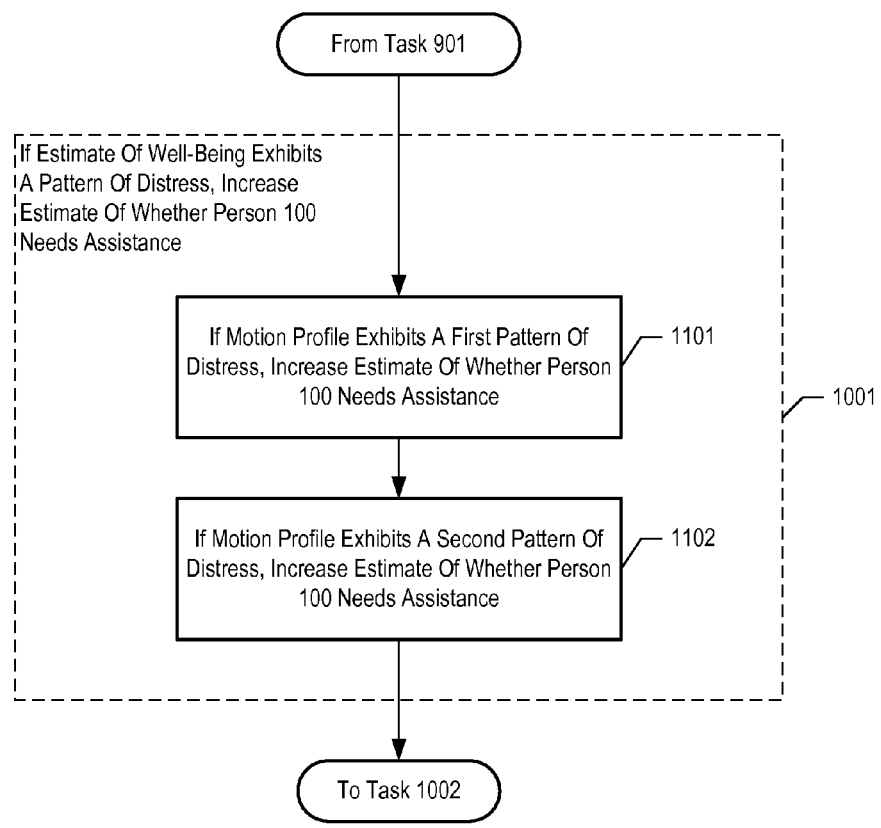
FIG. 11 depicts a flowchart of the salient tasks performed by processor 201 in task 901—increasing the parameter E—the estimate of whether person 100 needs assistance when the estimate of well-being exhibits a sign of distress by exhibiting a pattern of distress.

FIG. 11 depicts a flowchart of the salient tasks performed by processor 201 in task 1001—increasing the parameter E—the estimate of whether person 100 needs assistance when the estimate of well-being exhibits a sign of distress by exhibiting a pattern of distress.

At task 1101, processor 201 determines whether the motion profile in the estimate of well-being exhibits a first pattern of distress. In accordance with the illustrative embodiment, the first pattern of distress is designed to detect a fall by person 100. The estimate of well-being exhibits the first pattern of distress when both (i) and (ii), wherein:

(i) Either (A) or (B) or (A) and (B):

(A) the absolute value of the magnitude of any one value of $\overrightarrow{S1(c-14)}$ through $\overrightarrow{S1(c)}$ is less than 0.5 g followed by the absolute value of the magnitude of any one value of $\overrightarrow{S1(c-14)}$ through $\overrightarrow{S1(c)}$ is greater than 1.5 g, (B) the absolute value of the magnitude of any one value of $\overrightarrow{S2(c-14)}$ through $\overrightarrow{S2(c)}$ is less than 0.5 g followed by the absolute value of the magnitude of any one value of $\overrightarrow{S2(c-14)}$ through $\overrightarrow{S2(c)}$ is greater than 1.5 g; AND (ii) the estimate of attitude $\overrightarrow{\alpha(c)}$ that indicates that person 100 is not upright.

When processor 201 determines that the motion profile exhibits the first pattern of distress, the parameter E is increased by ten (10), which guarantees that the estimate of well-being of person 100 will indicate that person 100 does need assistance in task 803. It will be clear to those skilled in the art, after reading this disclosure, how to make and use alternative embodiments of the present invention that uses another pattern of distress to detect a fall by person 100.

At task 1102, processor 201 determines whether the motion profile in the estimate of well-being exhibits a second pattern of distress. In accordance with the illustrative embodiment, the second pattern of distress is a sinusoidal frequency component with a magnitude of greater than parameter B in M(c-1023) through M(c) having a frequency between 4 Hz and 11 Hz. It will be clear to those skilled in the art that this can be determined by performing a Fourier Transform on M(c-1023) through M(c). The second pattern of distress is designed to detect shivering, tremors, and shaking by person 100 and is an example of a sign of distress that is characterized by a parameter—the parameter B. When processor 201 determines that the motion profile exhibits the second pattern of distress, the parameter E is increased by the magnitude of the strongest sinusoidal frequency component divided by 0.00025. It will be clear to those skilled in the art, after reading this disclosure, how to make and use alternative embodiments of the present invention that use another pattern of distress to detect shivering, tremors, shaking, etc.

The illustrative embodiment tests for two patterns of distress—one periodic and one aperiodic—but it will be clear to those skilled in the art, after reading disclosure, how to make and use alternative embodiments of the present invention that test for any number of patterns of distress.

Figure 12:
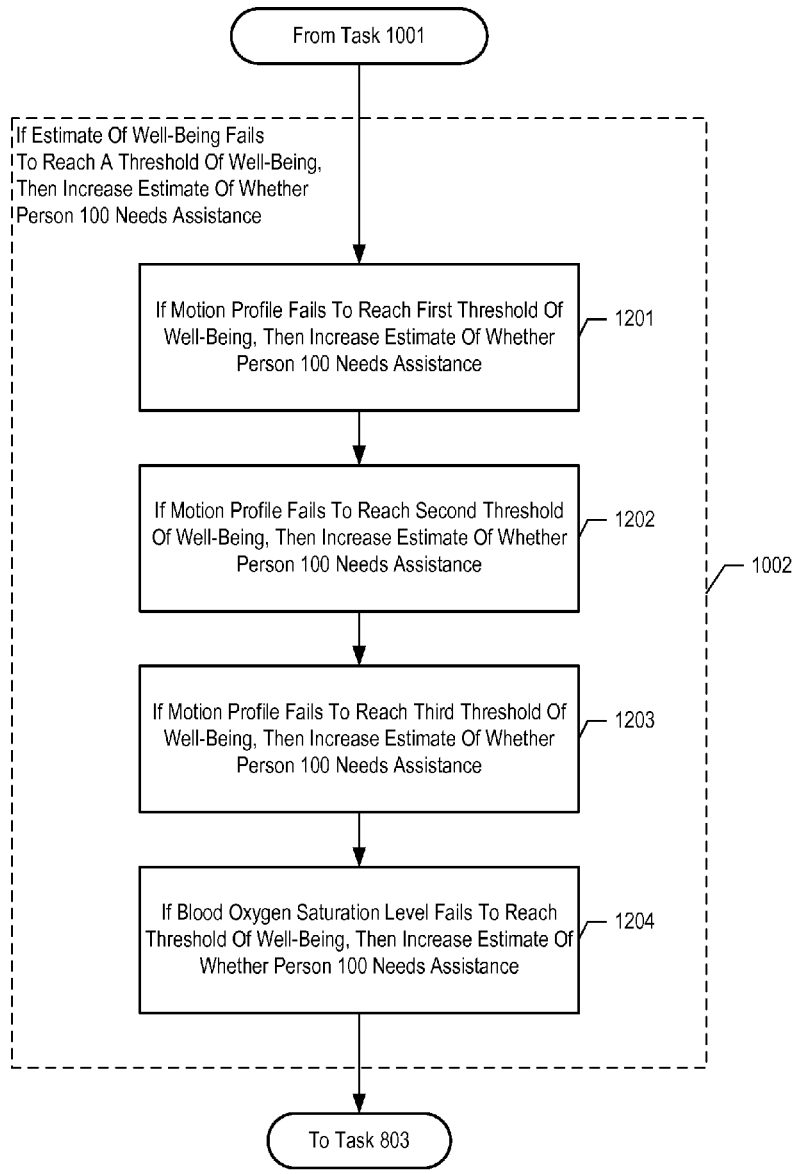
FIG. 12 depicts a flowchart of the salient tasks performed by processor 201 in task 10121—increasing the parameter E—the estimate of whether person 100 needs assistance when the estimate of well-being exhibits a sign of distress by failing to reach a threshold of well-being.

FIG. 12 depicts a flowchart of the salient tasks performed by processor 201 in task 1002—increasing the parameter E—the estimate of whether person 100 needs assistance when the estimate of well-being exhibits a sign of distress by failing to reach a threshold of well-being.

At task 1201, processor 201 determines if the motion profile in the estimate of well-being fails to reach the first threshold of well-being. To accomplish this, processor 201 generates:

$$E_1(k)=|A(k)-W_1| \tag{Eq. 6}$$

wherein k equals each value of z-$V_1$ through z, wherein:

$$V_1=f_1(T_1,\alpha(z),\beta(z),\delta(z),\phi(z),\omega(z),t,C(t)) \tag{Eq. 7}$$

and $$W_1=g_1(T_1,\alpha(z),\beta(z),\delta(z),\phi(z),\omega(z),t,C(t)) \tag{Eq. 8}$$

and wherein $T_1$ is the first threshold of well-being parameter and C(t) is a calendrical trait of time t. The purpose of the test in task 1202 is to quickly (e.g., within 30 seconds of an event that would require assistance for person 100, etc.) determine if person 100 is in need of assistance. The value of $V_1$ is nominally 75 (for 30 seconds of motion profile) but is increased as values of $\alpha$, $\beta$, and $\delta$, t, and C(t) suggest that person 100 is sleeping. The value of $W_1$ is nominally $T_1$ but is decreased as the blood oxygen saturation level $\phi$ of person 100 decreases. It will be clear to those skilled in the art, after reading this disclosure, how to make and use alternative embodiments of the present invention that use another test based on other functions and other inputs. If every value of $E_1(k)$ is negative, then the estimate of well-being fails to reach the first threshold of well-being and the parameter E is increased by ten (10).

At task 1202, processor 201 determines if the motion profile in the estimate of well-being fails to reach the second threshold of well-being. To accomplish this, processor 201 generates:

$$E_2(k)=|A(k)-W_2| \tag{Eq. 9}$$

wherein k equals each value of z-$V_2$ through z, wherein:

$$V_2=f_2(T_2,\alpha(z),\beta(z),\delta(z),\phi(z),\omega(z),t,C(t)) \tag{Eq. 10}$$

and $$W_2=f_2(T_2,\alpha(z),\beta(z),\delta(z),\phi(z),\omega(z),t,C(t)) \tag{Eq. 11}$$

and wherein $T_2$ is the second threshold of well-being parameter. The purpose of the test in task 1203 is to determine if person 100 is in need of assistance over a medium value of time. The value of $V_2$ is nominally 750 (for 5 minutes of motion profile) but is increased as values of $\alpha$, $\beta$, and $\delta$, t, and C(t) suggest that person 100 is sleeping. The value of $W_2$ is nominally $T_2$ but is decreased as the blood oxygen saturation level $\phi$ of person 100 decreases. It will be clear to those skilled in the art, after reading this disclosure, how to make and use alternative embodiments of the present invention that use another test based on other functions and other inputs. If every value of $E_2(k)$ is negative, then the estimate of well-being fails to reach the first threshold of well-being and the parameter E is increased by seven (7).

At task 1203, processor 201 determines if the motion profile in the estimate of well-being fails to reach the third threshold of well-being. To accomplish this, processor 201 generates:

$$E_3(k)=|A(k)-W_3| \tag{Eq. 12}$$

wherein k equals each value of z-$V_2$ through z, wherein:

$$V_3=4499 \tag{Eq. 13}$$

and $$W_3=f_3(T_3,\alpha(z),\beta(z),\delta(z),\phi(z),\omega(z),t,C(t)) \tag{Eq. 14}$$

and wherein $T_3$ is the third threshold of well-being parameter. The purpose of the test in task 1204 is to determine if person 100 is in need of assistance over a longer value of time. The value of $W_3$ is nominally $T_3$ but is decreased as the blood oxygen saturation level φ of person 100 decreases. It will be clear to those skilled in the art, after reading this disclosure, how to make and use alternative embodiments of the present invention that use another test based on other functions and other inputs. If every value of $E_3(k)$ is negative, then the estimate of well-being fails to reach the first threshold of well-being and the parameter E is increased by nine (9).

In accordance with the illustrative embodiment, the initial values of the thresholds of well-being parameters are set to a constant pre-determined value in task 501 and modified as described herein. It will be clear to those skilled in the art, however, after reading this disclosure, how to make and use alternative embodiments of the present invention in which one or more thresholds of well-being parameters are established empirically and on an ongoing basis. For example, processor 201 can continually analyze the person's measures of motion and use econometric analysis to determine the probability function of nominal values of the measures of motion, as a function of $\alpha(z),\beta(z),\delta(z),\phi(z),\omega(z),t,C(t)$. Then, processor 201 can establish a threshold of well-being parameter, for a given set of parameters $\alpha(z),\beta(z),\delta(z),\phi(z),\omega(z),t,C(t)$ at a value that is unlikely to occur when the person does not need assistance.

At task 1204, processor 201 determines if the blood oxygen saturation level $\phi(z)$ fails to reach a threshold of well-being. In accordance with the illustrative embodiment, the threshold of well-being for the blood oxygen saturation level is 94%. When processor 201 determines that the blood oxygen saturation level $\phi(z)$ is below 94%, then processor 201 increases the parameter by $104-\phi(z)$.

Figure 13:
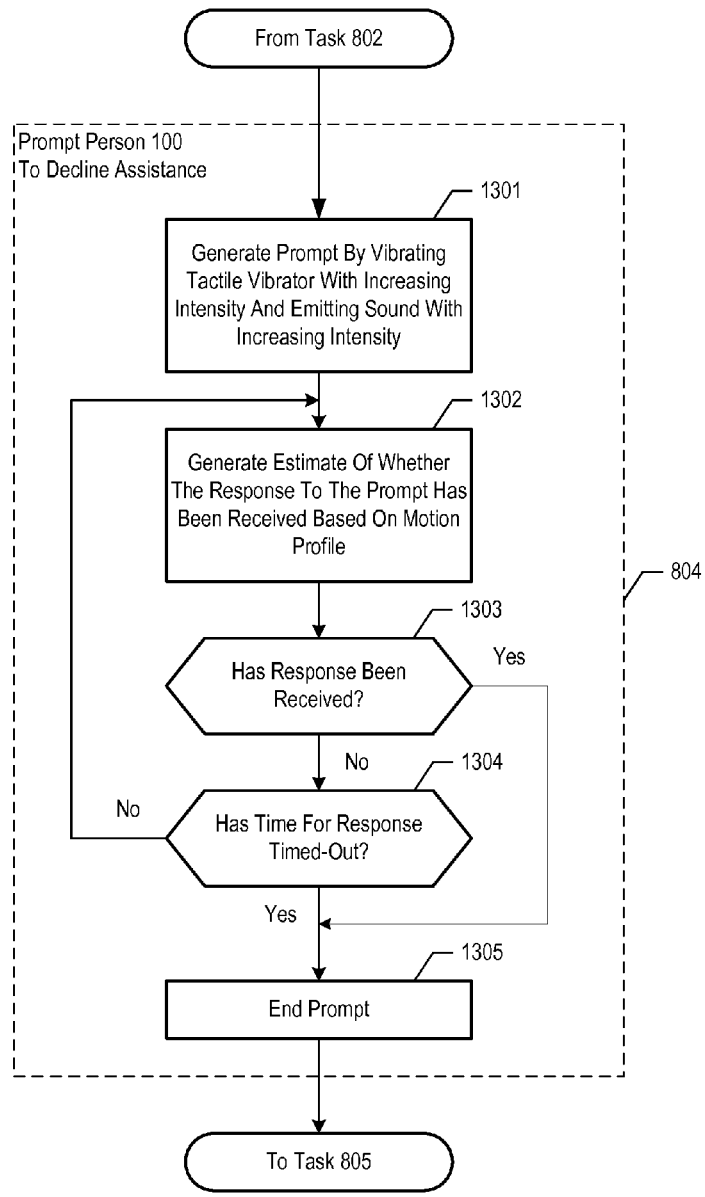
FIG. 13 depicts a flowchart of the salient tasks performed by processor 201 in task 804—prompting person 100 to decline assistance.

FIG. 13 depicts a flowchart of the salient tasks performed by processor 201 in task 804—prompting person 100 to decline assistance.

Figure 14:
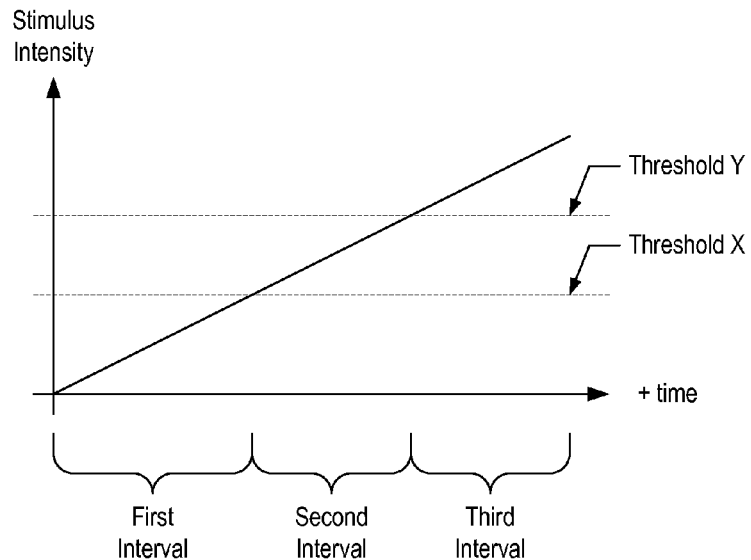
FIG. 14 depicts a graph of the intensity of the prompt as a function of time.

At task 1301, processor 201 generates a prompt for person 100 to decline assistance. In accordance with the illustrative embodiment, task 1301 is performed by: having processor 201 direct tactile vibrator 206, tactile vibrator 303-1, and tactile vibrator 303-2 to vibrate with increasing intensity, as depicted in FIG. 14. Initially and during the first time interval, the intensity of the vibration is below the threshold X. Because the threshold X is an estimate, the purpose of the first time interval is to prompt person 100 for 10 seconds and give him or her the highest chance to decline assistance without waking, if they are asleep.

Thereafter, during the second time interval, the intensity of the vibration is increased until it is above the threshold X and yet below the threshold Y. Because the threshold Y is an estimate, the purpose of the second interval is to prompt person 100 for 10 seconds and give him or her a reasonable chance to decline assistance without waking, if they are asleep.

Thereafter, during the third time interval, the intensity of the vibration is increased until it is above the threshold Y. The purpose of the third time interval is to prompt person for 10 seconds and give him or her a last chance to decline assistance. The vibration is clearly annoying during the third time interval, and, therefore, if the person does not respond during the third time interval he or she is clearly not responsive, and, therefore, in need of assistance.

As part of task 1301, processor 201 directs speaker 208 to output an acoustic signal with increasing intensity, as depicted in FIG. 14. The acoustic signal crosses the threshold X at the same time that the intensity of vibration crosses the threshold X, and the acoustic signal crosses the threshold Y at the same time that the intensity of the vibration crosses the threshold Y.

A parameter S is set to the value of c when task 1301 begins. As soon as task 1301 begins, task 1302 begins and task 1301 continues until ended by task 1305.

At task 1302, processor 201 generates an estimate of whether a response to the prompt has been received based on the motion profile generated since task 1301 began. Recall that task 502 is performed continually and concurrently with task 503, and, therefore, processor 201 is receiving measures of motion and generating motion profiles continually during task 804.

In accordance with the illustrative embodiment, person 100 responds to the prompt and declines assistance by moving or shaking either ancillary unit 302-1 or ancillary unit 302-2 or both. This motion is then reflected in the motion profile generated since task 1301 began.

Because the consequences of a false negative error are so high, the amount of motion deemed sufficient to constitute a response to decline assistance must be significant. Therefore, in accordance with the illustrative embodiment, processor 201 generates an estimate of whether the response to the prompt has been received by determining whether any value of A(S) through A(z) exceeds $T_3$. It will be clear to those skilled in the art, after reading this disclosure, how to make and use alternative embodiments of the present invention in which another test is used to estimate whether the response to the prompt has been received.

At task 1303, when the estimate of whether the response has been received exhibits a response, then control proceeds to task 1305; otherwise control proceeds to task 1304.

At task 1304, when a timer for receiving a response has timed out (i.e., the end of the third time interval in FIG. 14), then control proceeds to task 1305; otherwise control proceeds back to task 1302.

At task 1305, processor 201 ends the prompt and control proceeds to task 805.

Figure 15:
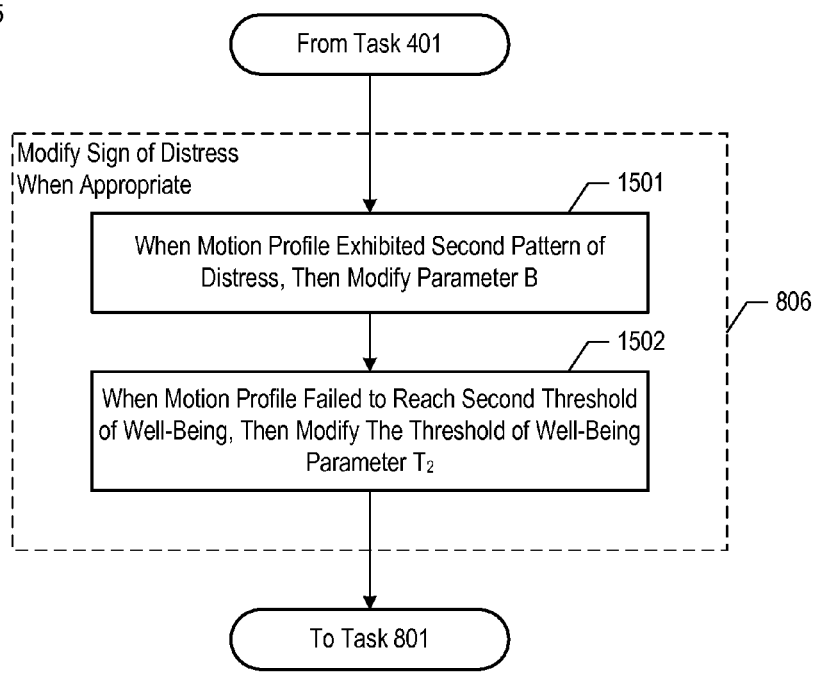
FIG. 15 depicts a flowchart of the salient tasks performed by processor 201 in task 806—modifying a sign of distress, when appropriate.

FIG. 15 depicts a flowchart of the salient tasks performed by processor 201 in task 806—modifying a sign of distress, when appropriate. The purpose of task 806 is to modify or adapt some of the signs of distress to reduce the number of false positive decisions that the illustrative embodiment makes in task 803.

When task 806 is reached because the motion profile exhibited a sign of distress by exhibiting the second pattern of distress, processor 201 at task 1501 increases the value of B by 1%.

When task 806 is reached because the motion profile exhibited a sign of distress by failing to reach the second threshold of well-being, processor 201 at task 1502 increases the value of $T_2$ by 1%.

Figure 16:
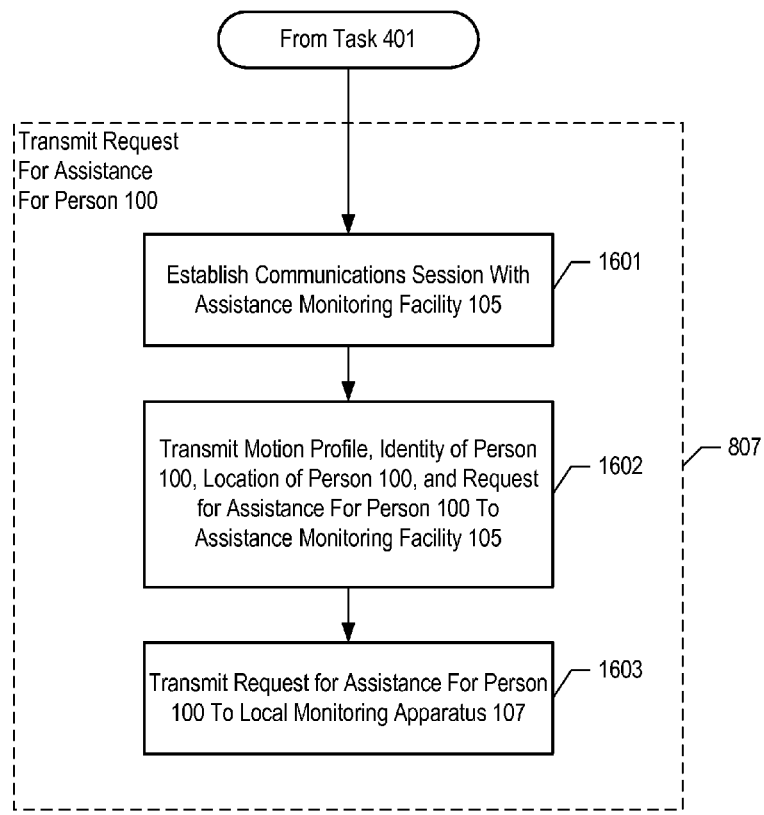
FIG. 16 depicts a flowchart of the salient tasks performed by processor 201 in task 807—transmitting a request for assistance for person 100.

FIG. 16 depicts a flowchart of the salient tasks performed by processor 201 in task 807—transmitting a request for assistance for person 100.

At task 1601, processor 201 directs radio transmitter and receiver 210 to direct cell phone 103 to initiate a communications session with assistance monitoring facility 105.

At task 1602, processor 201 transmits estimate of well-being, the motion profile, the parameters $\alpha(z),\beta(z),\delta(z),\phi(z),\omega(z),t,C(t)$, B, and $T_2$, to assistance monitoring facility 105 along with the identity of master unit 101, the location of master unit 101, the identity of person 100, and a request for assistance for person 100.

At task 1603, processor 201 directs radio transmitter and receiver 210 to direct local monitoring apparatus 107 to sound alarm 404, which is a local request for assistance for person 100.

Figure 17:
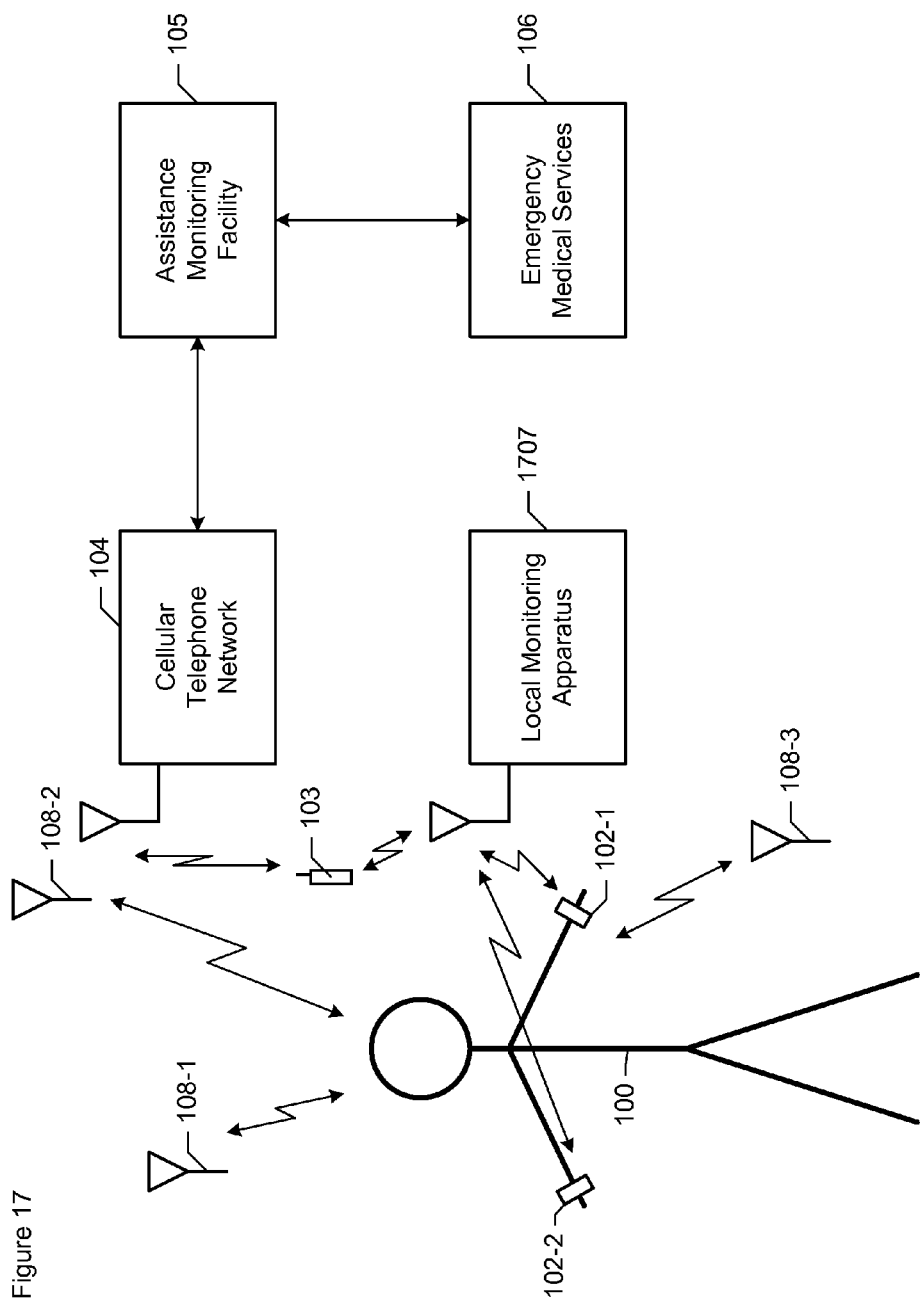
FIG. 17 depicts a schematic diagram of the first alternative embodiment of the present invention, which is used in conjunction with person 100.

FIG. 17 depicts a schematic diagram of the first alternative embodiment of the present invention, which is used in conjunction with person 100.

In accordance with the first alternative embodiment, there is no master unit 101. In accordance with the first alternative embodiment, ancillary units 102-1 and 102-2 perform the same functions as they did in the illustrative embodiment, and local monitoring apparatus 1707 performs the functions performed by master unit 101 in the illustrative embodiment, except that some or all of attitude sensor 202, microphone 203, light sensor 204, pulse oximeter 205, display 207, speaker 208, panic button 209, and location finder 211 are incorporated into ancillary unit 102-1 or ancillary unit 102-2 or are incorporated into local monitoring apparatus 1707 or are omitted altogether.

Figure 18:
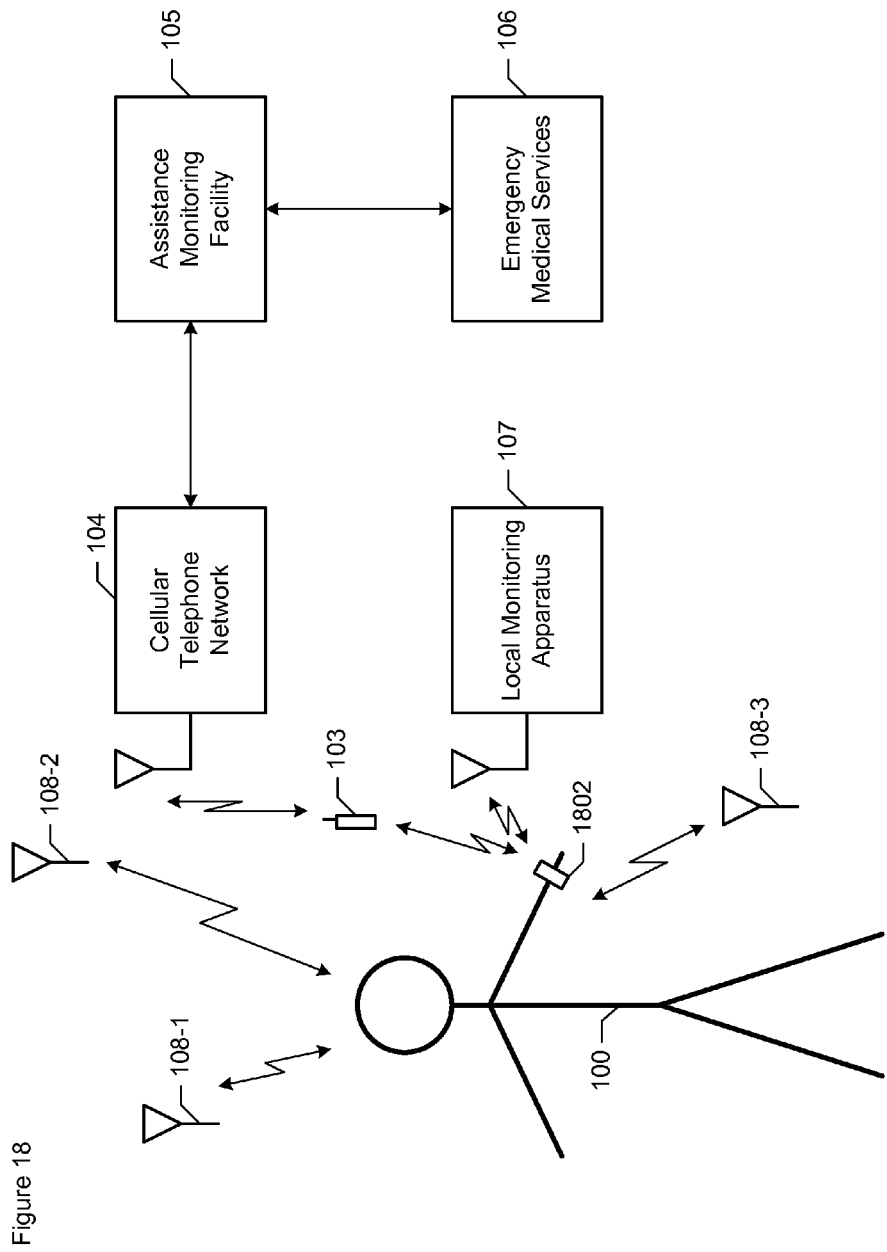
FIG. 18 depicts a schematic diagram of the second alternative embodiment of the present invention, which is used in conjunction with person 100.

FIG. 18 depicts a schematic diagram of the second alternative embodiment of the present invention, which is used in conjunction with person 100.

In accordance with the second alternative embodiment, one unit—monitoring unit 1802—performs the functionality of both master unit 101 and ancillary unit 102-1, and there is no ancillary unit 102-2. Local monitoring apparatus 107 is identical to that in the illustrative embodiment.

Figure 19:
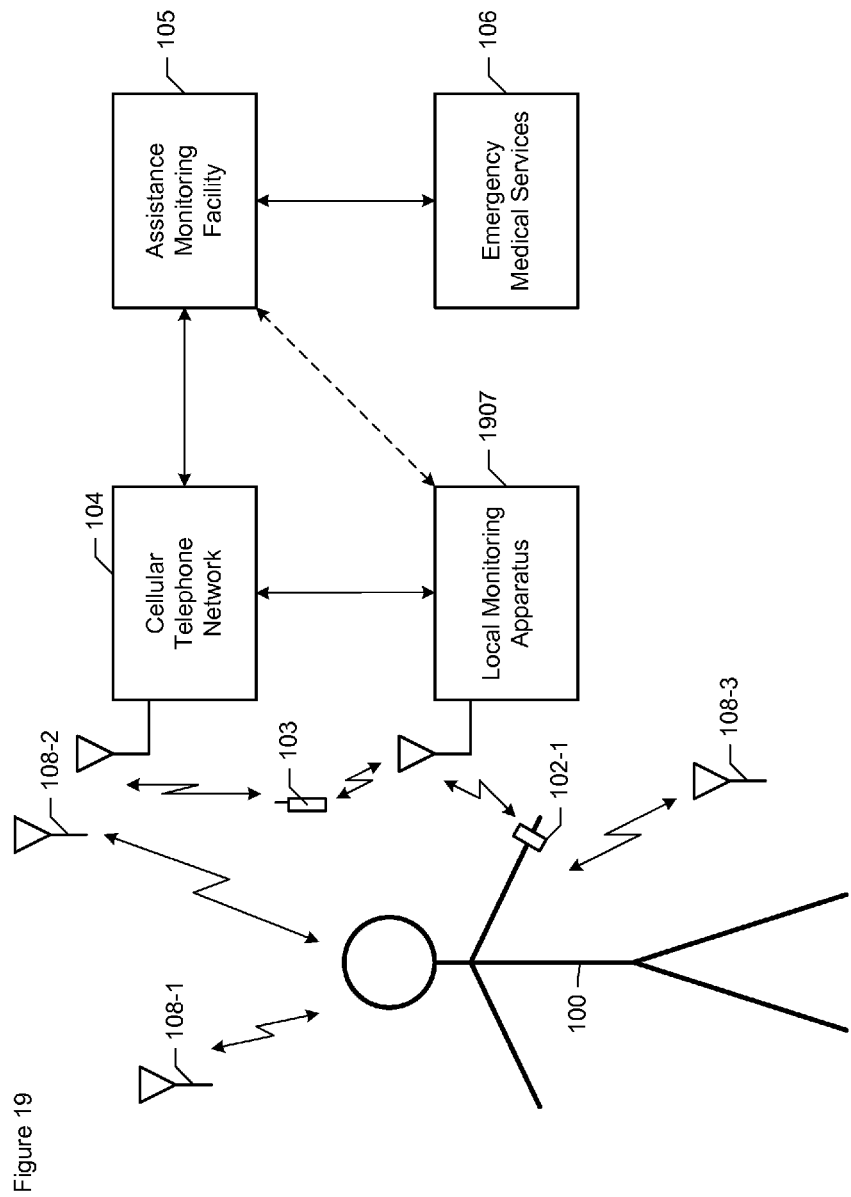
FIG. 19 depicts a schematic diagram of the third alternative embodiment of the present invention, which is used in conjunction with person 100.

FIG. 19 depicts a schematic diagram of the third alternative embodiment of the present invention, which is used in conjunction with person 100.

In accordance with the third alternative embodiment, there is only one ancillary unit, ancillary unit 102-1, which performs the same functions as it did in the illustrative embodiment. There is no master unit 101, and ancillary unit 102-1 interacts with local monitoring apparatus 1907, which performs the functions performed by master unit 101 in the illustrative embodiment, except that some or all of attitude sensor 202, microphone 203, light sensor 204, pulse oximeter 205, display 207, speaker 208, panic button 209, and location finder 211 are incorporated into ancillary unit 102-1 or ancillary unit 102-2 or are incorporated into local monitoring apparatus 1907 or are omitted altogether. And still furthermore, local monitoring apparatus 1907 has a wireline connection to assistance monitoring facility 105 that it can use rather than use cell phone 103.

FIG. 20 depicts a schematic diagram of the fourth alternative embodiment of the present invention, which is used in conjunction with person 100.

In accordance with the third alternative embodiment, there is only one ancillary unit, ancillary unit 102-1, which performs the same functions as it did in the illustrative embodiment. Cell phone 103, which is a "smart" phone performs all of the processing functions performed by processor 201 in the illustrative embodiment.

Markman Definitions

Accelerometer—For the purposes of this specification, an "accelerometer" is defined as hardware or hardware and software that measures:
 (i) the magnitude, or
 (ii) the direction, or
 (iii) the magnitude and the direction
of acceleration in one, two, or three dimensions.

Attitude sensor—For the purposes of this specification, an "attitude sensor" is defined as hardware or hardware and software that generates a one, two, or three-dimensional measure of the angular orientation or "attitude" of a person. The attitude sensor described in the illustrative embodiment might have more limitations than an attitude sensor in the claims.

Based on—For the purposes of this specification, the phrase "based on" is defined as "being dependent on" in contrast to "being independent of". Being "based on" includes both functions and relations.

Calendrical trait—For the purposes of this specification, a "calendrical trait" of time t is defined as a characterization of the time t. In this specification, a calendrical trait of time t is designated as C(t). For example and without limitation, the calendrical traits of time t include the day of the week, the day of the month, the month of the year, the season of the year, whether it is daytime or nighttime, whether t falls on a holiday, etc.

Cell phone—For the purposes of this specification, a "cell phone" should be given the ordinary and customary meaning that the terms would have to a person of ordinary skill in the art at the time of the invention. A cell phone is a synonym for a mobile station (in 3GPP nomenclature).

Display—For the purposes of this specification, a "display" is defined as hardware or hardware and software that converts an electromagnetic signal that might or might not be visible to a human eye into an electromagnetic signal that is visible to a human eye. The display described in the illustrative embodiment might have more limitations than a display in the claims.

Estimate of Well-Being—For the purposes of this specification, an "estimate of well-being" is defined as a characterization of the:
 (i) physical status, or
 (ii) mental status, or
 (iii) physical status and mental status
of a person.

Estimate of attitude—For the purposes of this specification, an "estimate of attitude" is defined as a one, two, or three-dimensional measure of the angular orientation or physical uprightness of a person. A person who standing straight upright has a different attitude than a person who is lying prone or supine.

Failure to reach a threshold of well-being—For the purposes of this specification, a "failure to reach a threshold of well-being" is defined as a level of activity of a person that suggests the person needs assistance.

Light sensor—For the purposes of this specification, a "light sensor" is defined as hardware or hardware and software that converts a light level into an electromagnetic signal. The light sensor described in the illustrative embodiment might have more limitations than a light sensor in the claims.

Limb—For the purposes of this specification, a "limb" is defined as an arm or leg.

Location finder—For the purposes of this specification, a "location finder" is defined as hardware or hardware and software that is capable of determining a location in one, two, or three dimensions. The location finder described in the illustrative embodiment might have more limitations than a location finder in the claims.

Location on a person's body—For the purposes of this specification, the phrase "location on a person's body" is defined as a point or region inside or on the surface of a person's body.

Measure of acceleration—For the purposes of this specification, a "measure of acceleration" is defined as:
 (i) the magnitude, or
 (ii) the direction, or
 (iii) the magnitude and the direction of acceleration in one, two, or three dimensions.

Measure of motion—For the purposes of this specification, a "measure of motion" is defined as:
(i) the magnitude, or
(ii) the direction, or
(iii) the magnitude and the direction
of:
(a) acceleration, or
(b) velocity
in one, two, or three dimensions.

Microphone—For the purposes of this specification, a "microphone" is defined as hardware or hardware and software that converts an acoustic vibration into an electromagnetic signal. The microphone described in the illustrative embodiment might have more limitations than a microphone in the claims.

Motion profile—For the purposes of this specification, a "motion profile" is defined as data and/or statistics regarding the motion of a person.

Motion sensor—For the purposes of this specification, a "motion sensor" is defined as hardware that directly measures:
(i) the magnitude, or
(ii) the direction, or
(iii) the magnitude and the direction
of at least one of:
(a) acceleration, or
(b) velocity
in one, two, or three dimensions.

Output device—For the purposes of this specification, an "output device" is defined as hardware or hardware and software that transmits a signal.

Panic button—For the purposes of this specification, a "panic button" is defined as hardware or hardware and software that when activated directs the transmission of a request for assistance. The panic button described in the illustrative embodiment might have more limitations than a panic button in the claims.

Pattern of distress—For the purposes of this specification, a "pattern of distress" is defined as a pattern in an estimate of well-being that suggests that a person 100 is in need of assistance. Some patterns of distress are periodic and detect, for example and without limitation, tremors, shuddering, shivering, etc. Some patterns of distress are not periodic and detect, for example and without limitation, falls, etc.

Processor—For the purposes of this specification, a "processor" is defined as hardware or hardware and software that performs mathematical and/or logical operations. The processor described in the illustrative embodiment might have more limitations than a processor in the claims.

Pulse oximeter—For the purposes of this specification, a "pulse oximeter" is defined as hardware or hardware and software that measures a blood oxygen saturation level and converts it into an electromagnetic signal. The pulse oximeter described in the illustrative embodiment might have more limitations than a pulse oximeter in the claims.

Radio—For the purposes of this specification, a "radio" is defined as hardware or hardware and software that is capable of telecommunications via an unguided (i.e., wireless) electromagnetic signal. The radio described in the illustrative embodiment might have more limitations than a radio in the claims.

Sign of distress—For the purposes of this specification, a "sign of distress" is defined as:
(i) a pattern of distress, or
(ii) a failure to reach a threshold of well-being.

Speaker—For the purposes of this specification, a "speaker" is defined as hardware or hardware and software that converts an electromagnetic signal into an acoustic vibration. The speaker described in the illustrative embodiment might have more limitations than a speaker in the claims.

Tactile vibrator—For the purposes of this specification, a "tactile vibrator" is defined as hardware or hardware and software that vibrates under the control of an electromagnetic signal. The tactile vibrator described in the illustrative embodiment might have more limitations than a tactile vibrator in the claims.

Threshold of well-being—For the purposes of this specification, a "threshold of well-being" is defined as a level of activity of a person that, when attained, suggests that the person does not need assistance.

To Exhibit—For the purposes of this specification, the infinitive "to exhibit" and its inflected forms (e.g., "exhibiting", "exhibits", etc.) is defined as "to manifest or make evident."

To Generate—For the purposes of this specification, the infinitive "to generate" and its inflected forms (e.g., "generating", "generation", etc.) should be given the ordinary and customary meaning that the terms would have to a person of ordinary skill in the art at the time of the invention.

To Receive—For the purposes of this specification, the infinitive "to receive" and its inflected forms (e.g., "receiving", "received", etc.) should be given the ordinary and customary meaning that the terms would have to a person of ordinary skill in the art at the time of the invention.

To Transmit—For the purposes of this specification, the infinitive "to transmit" and its inflected forms (e.g., "transmitting", "transmitted", etc.) should be given the ordinary and customary meaning that the terms would have to a person of ordinary skill in the art at the time of the invention.

When—For the purposes of this specification, the word "when" is defined as "upon the occasion of."

What is claimed is:

1. A method comprising:
receiving, from a motion sensor, a first measure of motion of a location on a person's body;
generating, by a processor, a motion profile based on the first measure of motion;
when the motion profile exhibits a sign of distress, generating, with a first output device, a prompt for the person to decline assistance;
receiving, from the motion sensor, a second measure of motion;
generating an estimate of whether the person has declined assistance based on the second measure of motion; and
when the estimate of whether the person has declined assistance indicates that the person has failed to decline assistance, transmitting, with a second output device, a request for assistance for the person.

2. The method of claim 1 wherein the first output device is a tactile vibrator.

3. The method of claim 1 wherein the sign of distress is a pattern of distress.

4. The method of claim 3 wherein the pattern of distress is periodic.

5. A method comprising:
receiving, from a motion sensor, a first measure of motion of a location on a person's body;
generating, by a processor, a first motion profile based on the first measure of motion;
when the first motion profile exhibits a first sign of distress as characterized by a parameter, generating, with a first output device, a prompt for the person to decline assistance, wherein the first sign of distress suggests distress that is independent of a fall;

when the person declines assistance, modifying the parameter to generate a modified parameter;
receiving, from the motion sensor, a second measure of motion of the location on the person's body;
generating a second motion profile based on the second measure of motion; and
when the second motion profile exhibits a second sign of distress as characterized by the modified parameter, transmitting, with a second output device, a request for assistance for the person.

6. The method of claim 5 wherein the first output device is a tactile vibrator.

7. The method of claim 5 wherein the first sign of distress is a pattern of distress.

8. The method of claim 7 wherein the pattern of distress is periodic.

9. A method comprising:
receiving, from a motion sensor, a measure of motion of a location on a person's body;
generating, by a processor, an estimate of well-being based on the measure of motion;
when the estimate of well-being fails to reach a threshold of well-being, generating, with a first output device, a prompt for the person to decline assistance; and
when the person fails to decline assistance, transmitting, with a second output device, a request for assistance for the person;
wherein the threshold of well-being suggests distress that is independent of a fall.

10. The method of claim 9 wherein the first output device is a tactile vibrator.

11. The method of claim 9 further comprising:
receiving an estimate of the location of the person; and
wherein the estimate of well-being is also based on the estimate of the location of the person.

12. The method of claim 9 further comprising:
receiving a measure of ambient light level in the vicinity of the person; and
wherein the estimate of well-being is also based on the measure of ambient light level.

13. The method of claim 9 further comprising:
receiving a measure of ambient sound level in the vicinity of the person; and
wherein the estimate of well-being is also based on the measure of ambient sound level.

14. An apparatus comprising:
a first output device;
a second output device;
a motion sensor to:
(i) generate, at a first time $t_1$, a first measure of motion of a location on a person's body, and
(ii) generate, at a second time $t_2$ that is after $t_1$, a second measure of motion of the location; and
a processor to:
(i) generate a motion profile based on the first measure of motion,
(ii) when the motion profile exhibits a sign of distress, direct, after time $t_1$ and before time $t_2$, the first output device to prompt the person to decline assistance,
(iii) generate an estimate of whether the person has declined assistance based on the second measure of motion, and
(iv) when the estimate of whether the person has declined assistance indicates that the person has failed to decline assistance, direct the second output device to transmit a request for assistance for the person.

15. The apparatus of claim 14 wherein the first output device is a tactile vibrator.

16. The apparatus of claim 14 wherein the sign of distress is a pattern of distress.

17. The apparatus of claim 16 wherein the pattern of distress is periodic.

18. An apparatus comprising:
a first output device;
a second output device;
a motion sensor to:
(i) generate a first measure of motion of a location on a person's body,
(ii) generate a second measure of motion of the location of the person's body; and
a processor to:
(i) generate a first motion profile based on the first measure of motion,
(ii) when the first motion profile exhibits a first sign of distress as characterized by a parameter, direct the first output device to prompt the person to decline assistance,
(iii) when the person declines assistance, modify the parameter to generate a modified parameter,
(iv) generate a second motion profile based on the second measure of motion, and
(v) when the second motion profile exhibits a second sign of distress as characterized by the modified parameter, direct the second output device to transmit a request for assistance for the person;
wherein the first sign of distress suggests distress that is independent of a fall.

19. The apparatus of claim 18 wherein the first output device is a tactile vibrator.

20. The apparatus of claim 18 wherein the first sign of distress is a pattern of distress.

21. The apparatus of claim 20 wherein the pattern of distress is periodic.

22. An apparatus comprising:
a first output device;
a second output device;
a motion sensor to generate a measure of motion of a location on a person's body; and
a processor to:
(i) generate an estimate of well-being based on the measure of motion,
(ii) when the estimate of well-being fails to reach a threshold of well-being, direct the first output device to prompt the person to decline assistance, and
(iii) when the person fails to decline assistance, direct the second output device to transmit a request for assistance for the person;
wherein the threshold of well-being suggests distress that is independent of a fall.

23. The apparatus of claim 22 wherein the first output device is a tactile vibrator.

24. The apparatus of claim 22 further comprising:
a location finder to generate an estimate of the location of the person; and
wherein the estimate of well-being is also based on the estimate of the location of the person.

25. The apparatus of claim 22 further comprising:
a light sensor to measure an ambient light level in the vicinity of the person; and
wherein the estimate of well-being is also based on the measure of ambient light level.

26. The apparatus of claim 22 further comprising:
a microphone to measure an ambient sound level in the vicinity of the person; and
wherein the estimate of well-being is also based on the measure of ambient sound level.

* * * * *